United States Patent [19]

Pilkington

[11] Patent Number: 5,723,473

[45] Date of Patent: Mar. 3, 1998

[54] PROPENOIC ACID DERIVATIVES USEFUL AS FUNGICIDES

[75] Inventor: Brian Leslie Pilkington, Maidenhead, England

[73] Assignee: Zeneca Limited, London, England

[21] Appl. No.: 416,701

[22] PCT Filed: Sep. 22, 1993

[86] PCT No.: PCT/GB93/01990

§ 371 Date: Apr. 11, 1995

§ 102(e) Date: Apr. 11, 1995

[87] PCT Pub. No.: WO94/08968

PCT Pub. Date: Apr. 28, 1994

[30] Foreign Application Priority Data

Oct. 14, 1992 [GB] United Kingdom ............ 9221526

[51] Int. Cl.$^6$ .............. A01N 47/42; C07D 217/56; C07D 217/62; C07D 217/22

[52] U.S. Cl. ............ 514/307; 514/309; 514/310; 546/141; 546/142; 546/145; 546/334; 546/335; 546/300; 546/283; 546/174; 546/153; 544/298; 544/309; 544/311; 544/312; 544/313; 544/314; 544/315; 544/316; 544/317; 544/318; 544/319; 544/320; 544/321; 544/322; 544/323; 544/324; 544/325; 544/326; 544/327; 544/328; 544/329; 544/330; 544/331; 544/332; 544/333; 544/334; 544/335; 544/219; 548/267.4; 548/375.1; 560/39; 549/440

[58] Field of Search ................ 514/256, 307, 514/357, 309, 310; 546/145, 334, 335, 141, 142; 544/335

[56] References Cited

U.S. PATENT DOCUMENTS 5,055,471 10/1991 De Fraine ............... 514/255
5,439,910 8/1995 De Fraine ............... 514/256

FOREIGN PATENT DOCUMENTS

78167/91 12/1991 Australia.
0 426 460 5/1991 European Pat. Off..

Primary Examiner—Mark L. Berch
Assistant Examiner—Bruck Kifle
Attorney, Agent, or Firm—Marian T. Thomson

[57] ABSTRACT

A fungicidal compound of formula (I):

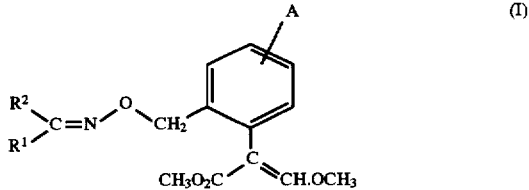

wherein A is hydrogen, halogen, hydroxy, $C_{1-4}$ alkyl, $C_{1-4}$ alkoxy, $C_{1-4}$ haloalkyl, $C_{1-4}$ haloalkoxy, $C_{1-4}$ alkylcarbonyl, $C_{1-4}$ alkoxycarbonyl, phenoxy, nitro or cyano; and one of $R^1$ and $R^2$ is optionally substituted isoquinoline while the other is hydrogen, $C_{1-4}$ alkyl, $C_{1-4}$ haloalkyl, halogen or cyano.

7 Claims, No Drawings

PROPENOIC ACID DERIVATIVES USEFUL AS FUNGICIDES

This invention relates to derivatives of propenoic acid useful as fungicides, to processes for preparing them, to compositions containing them, and to methods of using them to combat fungi, especially fungal infections of plants.

Fungicidal derivatives of propenoic acid including an oxime ether group, and having the general formula (I) are described in EP-A-0370629 and WO/GB92/00681 (published as WO92/18487), and these have the general formula (I) wherein A is hydrogen, halo, hydroxy, $C_{1-4}$ alkyl, $C_{1-4}$ alkoxy, $C_{1-4}$ haloalkyl, $C_{1-4}$ haloalkoxy, $C_{1-4}$ alkylcarbonyl, $C_{1-4}$ alkoxycarbonyl, phenoxy, nitro or cyano; $R^1$ and $R^2$, which may be the same or different, are hydrogen, optionally substituted alkyl, optionally substituted cycloalkyl, optionally substituted heterocyclylalkyl, optionally substituted cycloalkylalkyl, optionally substituted aralkyl, optionally substituted heteroarylalkyl, optionally substituted aryloxyalkyl, optionally substituted heteroaryloxyalkyl, optionally substituted alkenyl, optionally substituted alkynyl, optionally substituted alkoxy, optionally substituted aryl, optionally substituted heteroaryl, optionally substituted aryloxy, optionally substituted heteroaryloxy, nitro, halo cyano, —$NR^3R^4$, —$CO_2R^3$, —$CONR^3R^4$, —$COR^3$, —$S(O)_nR^3$ wherein n is 0, 1 or 2, $(CH_2)_mPO(OR^3)_2$ wherein m is 0 or 1, or $R^1$ and $R^2$ join to form a carbocyclic or heterocyclic ring system; and $R^3$ and $R^4$, which may be the same or different, are hydrogen, optionally substituted alkyl, optionally substituted aralkyl, optionally substituted alkenyl, optionally substituted alkynyl, optionally substituted aryl or optionally substituted heteroaryl.

The present invention provides a compound of formula (I) wherein either: A is hydrogen, halogen, hydroxy, $C_{1-4}$ alkyl, $C_{1-4}$ alkoxy, $C_{1-4}$ haloalkyl, $C_{1-4}$ haloalkoxy, $C_{1-4}$ alkylcarbonyl, $C_{1-4}$ alkoxycarbonyl, phenoxy, nitro or cyano; and one of $R^1$ and $R^2$ is optionally substituted isoquinoline while the other is hydrogen, $C_{1-4}$ alkyl, $C_{1-4}$ haloalkyl, halogen or cyano; or A is hydrogen, $R^2$ is methyl and $R^1$ is 4-tert-butylpyrid-2-yl, 4-tert-butylpyrimidin-2-yl, 5-methyl-6-iso-propoxypyrimidine-4-yl or 4-($C_{1-4}$ chlorofluoroalkyl)pyrid-2-yl (such as 4-$ClF_2C$-pyrid-2-yl or 4-$Cl_2FC$-pyrid-2-yl).

The compounds of the invention contain at least one carbon-nitrogen double bond and at least one carbon-carbon double bond, and are sometimes obtained in the form of mixtures of geometric isomers. However these mixtures can be separated into individual isomers, and this invention embraces such isomers, and mixtures thereof in all proportions.

The individual isomers which result from the unsymmetrically substituted double bond of the propenoate group and the oxime are identified by the commonly used terms "E" and "Z". These terms are defined according to the Cahn-Ingold-Prelog system which is fully described in the literature (see, for example, J March, "Advanced Organic Chemistry", 3rd edition, Wiley-Interscience, page 109 et seq).

For the carbon-carbon double bond of the propenoate group, usually one isomer is more active fungicidally than the other, the more active isomer usually being the one wherein the group —$CO_2CH_3$ and —$OCH_3$ are on opposite sides of the olefinic bond of the propenoate group (the (E)-isomer). These (E)-isomers form a preferred embodiment of this invention.

Substitutents which may be present in the optionally substituted isoquinoline moiety include one or more of the following: halogen, hydroxy, mercapto, $C_{1-4}$ alkyl (especially methyl and ethyl), $C_{2-4}$ alkenyl (especially allyl), $C_{2-4}$ alkynyl (especially propargyl), $C_{1-4}$ alkoxy (especially methoxy), $C_{2-4}$ alkenyloxy (especially allyloxy), $C_{2-4}$ alkynyloxy (especially propargyloxy), halo($C_{1-4}$)alkyl (especially trifluoromethyl), halo($C_{1-4}$)alkoxy (especially trifluoromethoxy), $C_{1-4}$ alkylthio (especially methylthio), halo($C_{1-4}$)alkylthio, hydroxy($C_{1-4}$)alkyl, $C_{1-4}$ alkoxy($C_{1-4}$) alkyl, $C_{3-6}$ cycloalkyl, $C_{3-6}$ cycloalkyl($C_{1-4}$)alkyl, optionally substituted methylenedioxy (especially optionally substituted with fluorine or $C_{1-4}$ alkyl), optionally substituted aryl (especially optionally substituted phenyl), optionally substituted heteroaryl (especially optionally substituted pyridyl or pyrimidinyl), optionally substituted heterocyclyl (especially optionally substituted pyrrolidine), optionally substituted aryloxy (especially optionally substituted phenoxy), optionally substituted heteroaryloxy (especially optionally substituted pyridyloxy or pyrimidinyloxy), optionally substituted aryl($C_{1-4}$)alkyl (especially optionally substituted benzyl, optionally substituted phenethyl and optionally substituted phenyl n-propyl) in which the alkyl moiety is optionally substituted with hydroxy, optionally substituted heteroaryl ($C_{1-4}$)alkyl (especially optionally substituted pyridyl- or pyrimidinyl($C_{1-4}$)alkyl), optionally substituted aryl($C_{2-4}$) alkenyl (especially optionally substituted phenylethenyl), optionally substituted heteroaryl($C_{2-4}$)alkenyl (especially optionally substituted pyridylethenyl or pyrimidinylethenyl), optionally substituted aryl($C_{1-4}$)alkoxy (especially optionally substituted benzyloxy), optionally substituted heteroaryl($C_{1-4}$)alkoxy (especially optionally substituted pyridyl- or pyrimidinyl($C_{1-4}$)alkoxy, optionally substituted aryloxy($C_{1-4}$)alkyl (especially phenoxymethyl), optionally substituted heteroaryloxy($C_{1-4}$)alkyl (especially optionally substituted pyridyloxy- or pyrimidinyloxy($C_{1-4}$) alkyl), acyloxy (including $C_{1-4}$ alkanoyloxy (especially acetyloxy) and benzoyloxy), cyano, thiocyanato, nitro, —NR'R", —NHCOR', —NHCONR'R", —CONR'R", —COOR', —OSO2R', —SO2R', —COR', —CR'=NR" or —N=CR'R" in which R' and R" are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy; when R' and R" are in CONR'R" they can together form a 5- or 6-membered heterocyclic ring (for example a pyrrole, imidazole, pyrrolidine, piperidine or morpholine ring); or two substituents, when they are in adjacent positions on the aryl or heteroaryl ring can join to form a fused alphatic ring (especially to form a fused 6-membered carbon aliphatic ring). Substituents which may be present in the aryl or heteroaryl rings of any of the foregoing substituents include one or more of the following: halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$) alkoxy, $C_{1-4}$ alkylthio, hydroxy($C_{1-4}$)alkyl, $C_{1-4}$ alkoxy ($C_{1-4}$) alkyl, $C_{3-6}$ cycloalkyl, $C_{3-6}$ cycloalkyl($C_{1-4}$)alkyl, alkanoyloxy, benzoyloxy, cyano, thiocyanato, nitro, —NR'R", —NHCOR', —NHCONR'R", —CONR'R", —COOR', —$SO_2R'$, —$OSO_2R'$, —COR', —CR'=NR" or —N=CR'R" in which R' and R" have the meanings given above.

Aryl includes naphthyl but is preferably phenyl. Heteroaryl includes 5- and 6-membered aromatic rings containing one, two or three heteroatoms selected from the list comprising oxygen, sulphur and nitrogen and can be fused to benzenoid ring systems. Examples of heteroaryl are pyridinyl, pyrimidinyl, pyridazinyl, pyrazinyl, triazinyl (1,2, 3-, 1,2,4- and 1,3,5-), furyl, thienyl, pyrrolyl, pyrazolyl, imidazolyl, triazolyl (1,2,3- and 1,2,4-), oxazolyl, isoxazolyl, thiazolyl, isothiazolyl, quinolinyl, isoquinolinyl, cinnolinyl, quinazolinyl, quinoxalinyl, indolinyl, isoindolinyl, benzofuranyl, benzothienyl and benzimidazolinyl.

All alkyl moieties, including the alkyl moiety of, for example, alkoxy and haloalkylthio, are in the form of straight or branched chains, and are, for example methyl, ethyl, n- or iso- propyl, or n-, sec-, iso- or tert-butyl.

Alkenyl and alkynyl moieties are in the form of straight or branched chains, and the alkenyl moieties, where appropriate, may have either the (E)- or (Z)-configuration. Examples are vinyl, allyl and propargyl.

Halogen is typically fluorine, chlorine or bromine.

It is preferred that $R^2$ is methyl, hydrogen or cyano.

The isoquinoline ring of $R^1$ or $R^2$ can be linked by any one of its carbon atoms, preferably it is linked through its 3-carbon (that is, it is an isoquinolin-3-yl moiety).

When substituted the isoquinoline ring of $R^1$ or $R^2$ is substituted on a ring carbon atom, preferably at the 5-position (that is, it is a 5-substituted isoquinolinyl moiety).

In one aspect the present invention provides compound of formula (I) wherein A is hydrogen, $R^2$ is methyl and $R^1$ is isoquinoline unsubstituted or substituted by one or more of halogen, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ haloalkylthio, $C_{1-4}$ hydroxyalkyl, $C_{1-4}$ alkoxy($C_{1-4}$)alkyl, $C_{1-4}$ alkoxy($C_{1-4}$) alkoxy($C_{1-4}$)alkyl, nitro cyano, COR', NR'R", OCOR' hydroxy, mercapto, $C_{2-4}$ alkenyl, $C_{2-4}$ alkynyl, $C_{2-4}$ alkenyloxy, $C_{2-4}$ alkynyloxy, $C_{3-6}$ cycloalkyl, $C_{3-6}$ cycloalkyl($C_{1-4}$)alkyl, NHCOR' or CONR'R"; R' and R" are, independently, hydrogen, $C_{1-4}$ alkyl, $C_{1-4}$ alkoxy, $C_{1-4}$ alkylthio, $C_{3-6}$ cycloalkyl or $C_{3-6}$ cycloalkyl($C_{1-4}$)alkyl or phenyl, phenoxy, benzyl or benzyloxy, the aromatic parts of which are optionally substituted by halogen, $C_{1-4}$ alkyl or $C_{1-4}$ alkoxy.

In another aspect the present invention provides a compound of formula (I) wherein A is hydrogen, $R^2$ is methyl and $R^1$ is isoquinoline unsubstituted or substituted by one or more of halogen (especially fluorine or chlorine), $C_{1-4}$ alkyl (especially methyl), $C_{1-4}$ alkoxy (especially methoxy or ethoxy), $C_{1-4}$ haloalkyl (especially $CF_3$) or $C_{1-4}$ haloalkoxy (especially $OCF_3$).

According to the present invention there are provided the individual (E)- and (Z)-isomers of Compounds Nos 694 to 885 or mixtures thereof in any proportion, having the formula (I) and the values of $R^1$, $R^2$ and A given in Table I.

TABLE I

| Compound No. | $R^1$ | $R^2$ | A | Olefinic+ | Melting Point °C. |
|---|---|---|---|---|---|
| 694 | 5-n-propyl-6-methoxy-pyrimidin-4-yl | $CH_3$ | H | 7.58 | gum |
| 695 | 4-cyclobutyl-$CH_2$O-pyrimidin-2-yl | $CH_3$ | H | 7.59 | gum |
| 696 | 6-OH-pyrimidin-4-yl | $CH_3$ | H | 7.60 | 172.6–173.5 |
| 697 | 5-$CH_3$O-pyrid-2-yl | $CH_3$ | H | 7.59 | gum |
| 698 | 6-allyloxy-pyrimidin-4-yl | $CH_3$ | H | 7.60 | gum |
| 699 | 5-$CH_3$-6-$CF_3$-pyrimidin-4-yl | $CH_3$ | H | 7.60 | gum |
| 700 | 5-n-propyl-6-$CH_3$C(E-NOH)-pyrimidin-4-yl | $CH_3$ | H | 7.59 | gum |
| 701 | 5-n-propyl-6-$CH_3$C(Z-NOH)-pyrimidin-4-yl | $CH_3$ | H | 7.59 | gum |
| 702 | Pyrid-4-yl-$CH_2$ | $CH_3$ | H | 7.58 | gum |
| 703 | Isoquinolin-1-yl | $CH_3$ | H | 7.60 | 96–98.2 |
| 704 | 6-$CH_3$C(E-NOH)-pyrimidin-4-yl | $CH_3$ | H | 7.61 | 190.4–190.7 |
| 705 | 1,2,4-triazol-1-yl-$CH_2$ | $CH_3$ | H | 7.59 | gum |
| 706 | 4-vinyl-pyrimidin-2-yl | $CH_3$ | H | 7.58 | gum |
| 707 | 6-$CH_3$C(E-NO$CH_3$)-pyrimidin-4-yl | $CH_3$ | H | 7.62 | 128–9 |
| 708 | 4-$CH_3CH_2OCH_2CH_2CH_2$O-pyrimidin-2-yl | $CH_3$ | H | 7.58 | gum |
| 709 | 3-$CH_3$-pyrimidin-2-yl-4-one | $CH_3$ | H | 7.58 | gum |
| 710 | 4-$CF_3CH_2$S-pyrimidin-2-yl | $CH_3$ | H | 7.58 | gum |
| 711 | 4-Cl-pyrimidin-2-yl | $CH_3$ | H | 7.58 | gum |
| 712 | Pyrazol-1-yl-$CH_2CH_2$ | $CH_3$ | H | 7.59 | gum |
| 713 | 6-propargyloxy-pyrimidin-4-yl | $CH_3$ | H | 7.60 | gum |
| 714 | 4-iso-propyloxy-5-$CH_3$O-pyrimidin-2-yl | $CH_3$ | H | 7.58 | 101–103 |
| 715 | 5-n-propyl-6-propargyloxy-pyrimidin-4-yl | $CH_3$ | H | 7.58 | gum |
| 716 | 4-OH-5-$CH_3$O-pyrimidin-2-yl | $CH_3$ | H | 7.61 | 170–172 |
| 717 | 4-$CH_3OCH_2$-pyrimidin-2-yl | $CH_3$ | H | 7.57 | 106–108 |
| 718 | 4,6-di-$CH_3$-pyrimidin-2-yl | $NH_2$ | H | 7.56 | gum |
| 719 | 4,6-di-$CH_3$-pyrimidin-2-yl | Cl | H | 7.59 | gum |
| 720 | 4,6-di-$CH_3$-pyrimidin-2-yl | $SCH_3$ | H | 7.55 | gum |
| 721 | 6-$C_2H_5$OC(=$CH_2$)-pyrimidin-4-yl | $CH_3$ | H | 7.60 | 106–107 |
| 722 | Pyrid-1-yl-2-one-$CH_2$ | $CH_3$ | H | 7.59 | gum |
| 723 | 4-n-propyl-pyrimidin-2-yl | $CH_3$ | H | 7.58 | 92–94 |
| 724 | Quinazolin-4-yl | $CH_3$ | H | 7.60 | 143.2–143.6 |
| 725 | 4-$CF_3CH_2$O-5,6-di-$CH_3$-pyrimidin-2-yl | $CH_3$ | H | 7.58 | 111 |
| 726 | 4-$CH_3$O-5,6-di-$CH_3$-pyrimidin-2-yl | $CH_3$ | H | 7.58 | 137.6 |
| 727 | 5-Cl-6-$C_2H_5$O-pyrimidin-4-yl | $CH_3$ | H | 7.59 | 84.8–86.4 |
| 728 | Quinolin-2-yl | $CH_3$ | H | 7.61 | 109.5–110.2 |
| 729 | 4-n-propyl-6-$C_2H_5$O-pyrimidin-2-yl | $CH_3$ | H | 7.58 | 66–68 |

TABLE I-continued

| Compound No. | R¹ | R² | A | Olefinic+ | Melting Point °C. |
|---|---|---|---|---|---|
| 730 | 4-CF₃-6-C₂H₅O-pyrimidin-2-yl | CH₃ | H | 7.58 | 115.3 |
| 731* | Cyclohexyl | | H | 7.56 | gum |
| 732 | 5-CH₃-6-CH₃O-pyrimidin-4-yl | CH₃ | H | 7.55 | 127–128.1 |
| 733 | 5-CH₃-6-C₂H₅O-pyrimidin-4-yl | CH₃ | H | 7.58 | 98.5–99.6 |
| 734 | φ | | | 7.59 | 136.1–136.5 |
| 735 | 5-CH₃-6-iso-propyloxy-pyrimidin-4-yl | CH₃ | H | 7.59 | 56.3–58.3 |
| 736 | 4-C₂H₅-6-C₂H₅O-pyrimidin-2-yl | CH₃ | H | 7.59 | 62–64 |
| 737 | 4-Cl-isoquinolin-1-yl | CH₃ | H | 7.60 | gum |
| 738 | 4-C₆H₅-pyrimidin-2-yl | CH₃ | H | 7.58 | 97 |
| 739* | Cyclopentyl | | H | 7.55 | gum |
| 740 | 5-Cl-6-CF₃CH₂O-pyrimidin-4-yl | CH₃ | H | 7.58 | gum |
| 741* | Indan-2-one | | H | 7.58 | 112–114 |
| 742 | 2-CH₃C(E-NOH)-pyrimidin-4-yl | CH₃ | H | 7.61 | 202 |
| 743 | φ | | | 7.59 | gum |
| 744 | φ | | | 7.60 | gum |
| 745 | 4-CHF₂O-pyrimidin-2-yl | CH₃ | H | 7.59 | 93–95 |
| 746 | 4-CH₂=CH-pyrimidin-2-yl | CH₃ | H | 7.58 | gum |
| 747 | 5-Cl-6-C₂H₅-pyrimidin-4-yl | CH₃ | H | 7.58 | gum |
| 748 | 6-Cl-quinazolin-2-yl | CH₃ | H | 7.58 | 141.2–143 |
| 750 | 4-C₂H₅OCH₂-pyrimidin-2-yl | CH₃ | H | 7.58 | 64–66 |
| 751 | 4-CH₂=CHCH₂-pyrimidin-2-yl | CH₃ | H | 7.59 | gum |
| 752 | 4-CH₂=C(OC₂H₅)-pyrimidin-2-yl | CH₃ | H | 7.59 | 94–95 |
| 753 | 4-CH₃CO-pyrimidin-2-yl | CH₃ | H | 7.59 | 104–106 |
| 754 | 4-(CH₃)₃C-pyrimidin-2-yl | CH₃ | H | 7.56 | 136 |
| 755 | 4-cyano-pyrimidin-2-yl | CH₃ | H | 7.59 | 90–92 |
| 756 | 4-C₂H₅OCH₂-6-CF₃CH₂O-pyrimidin-2-yl | CH₃ | H | 7.58 | 90–92 |
| 757 | 4-C₂H₅O-quinolin-2-yl | CH₃ | H | 7.61 | 149.5 |
| 758 | 4-CH(CH₃)₂-Pyrimidin-2-yl | CH₃ | H | 7.58 | 97.98 |
| 759 | 4-(CH₃)₂CHO-5,6-di-CH₃-pyrimidin-2-yl | CH₃ | H | 7.58 | 78–80 |
| 760 | φ | | | 7.59 | 129.0–134.4 |
| 761 | φ | | | 7.61 | gum |
| 762 | 2-CH₃-4,6-di-CH₃O-pyrimidin-5-yl | CH₃ | H | 7.57 | gum |
| 763 | 4-CH₃CF₂-pyrimidin-2-yl | CH₃ | H | 7.58 | 96–97 |
| 764 | 4,5-(CH₂)₃-pyrimidin-2-yl | CH₃ | H | 7.57 | gum |
| 765 | 6-(CH₃)₃C-pyrimidin-4-yl | CH₃ | H | 7.60 | gum |
| 766 | 5-CH₂=CH-pyrimidin-2-yl | CH₃ | H | 7.59 | 109–111 |
| 767 | 4-cyclopropyl-pyrimidin-2-yl | CH₃ | H | 7.56 | 90–92 |
| 768 | Isoquinolin-4-yl | CH₃ | H | 7.60 | 93.4–94.4 |
| 769 | 3,4-OCH₂O-C₆H₃ | CH₃ | H | 7.60 | gum |
| 770 | 3,4-di-CH₃O-C₆H₃ | CH₃ | H | 7.59 | gum |
| 771 | 5-CH(CH₃)₂-6-CH₃-pyrimidin-4-yl | CH₃ | H | 7.56 | 119.5–120.2 |
| 772 | φ | | | 7.53 | gum |
| 773 | 3-CF₃-C₆H₄ | CHF₂ | H | 7.60 | gum |
| 774 | 5,6-SCH₂CH₂-pyrimidin-4-yl | CH₃ | H | 7.60 | 116.3–116.9 |
| 775 | 5,6-CH₂SCH₂CH₂-pyrimidin-4-yl | CH₃ | H | 7.59 | 119.9–120.6 |
| 776 | 3-CH₃O-C₆H₄ | CHF₂ | H | 7.60 | gum |
| 777 | 4-C₂F₅-pyrimidin-2-yl | CH₃ | H | 7.58 | 115–117 |
| 778 | 4-C₂H₅O-pyrimidin-2-yl | H | H | 7.58 | 89–90 |
| 779 | 4-C₂H₅O-6-CH₃-1,3,5-triazin-2-yl | CH₃ | H | 7.58 | gum |
| 780 | 5,6-CH₂CH₂SCH₂-pyrimidin-4-yl | CH₃ | H | 7.54 | gum |
| 781 | 5,6-CH₂S(O)CH₂CH₂-pyrimidin-4-yl | CH₃ | H | 7.61 | 138.3–139.1 |
| 782 | 5,6-CH₂S(O₂)CH₂CH₂-pyrimidin-4-yl | CH₃ | H | 7.60 | 176.9–177.8 |
| 783 | 4-CF₃(CF₂)₂-pyrimidin-2-yl | CH₃ | H | 7.59 | 89–91 |
| 784 | 3-CH₃-C₆H₄ | CHF₂ | H | 7.60 | gum |
| 785 | 5,6-CH₂SCH₂-pyrimidin-4-yl | CH₃ | H | 7.59 | 117.2–117.9 |
| 786 | 4-(pyrid-2-yl)-pyrimidin-2-yl | CH₃ | H | 7.59 | 88–90 |
| 787 | 5,6-(CH₂)₄-pyrimidin-4-yl | CH₃ | H | 7.58 | 93.0–93.8 |
| 788 | 4-CH(CH₃)₂O-pyrimidin-2-yl | H | H | 7.59 | gum |
| 789 | 4-C₂F₅-5-Cl-pyrimidin-2-yl | CH₃ | H | 7.58 | gum |
| 790 | 5-C₂H₅-pyrimidin-2-yl | CH₃ | H | 7.58 | 99–101 |
| 791 | 6,7-di-CH₃O-iso-quinolin-1-yl | CH₃ | H | 7.58 | 172.8–173.8 |
| 792 | 5,6-(CH₂)₃-pyrimidin-4-yl | CH₃ | H | 7.60 | 96.9–97.7 |
| 793 | Isoquinolin-3-yl | CH₃ | H | 7.60 | 97.0–98.0 |
| 794 | Quinolin-4-yl | H | H | 7.63 | gum |
| 795 | 4-CF₂Cl-pyrid-2-yl | CH₃ | H | 7.61 | gum |
| 796 | 4-C(CH₃)₃-5-Cl-pyrimidin-2-yl | CH₃ | H | 7.58 | 124–126 |
| 797 | Quinolin-4-yl | CH₃ | H | 7.60 | oil |
| 798 | Quinolin-2-yl | H | H | 7.61 | 108.4–109.8 |
| 799 | φ | | | 7.64 | 180.0–184.4 |
| 800 | 4-[CH₃OC(CH₃)₂]-pyrimidin-2-yl | CH₃ | H | 7.59 | oil |
| 801 | 4-CF₃-5-CH₃-pyrimidin-2-yl | CH₃ | H | 7.60 | 79–80 |
| 802 | 4-CF₃-5-Cl-pyrimidin-2-yl | CH₃ | H | 7.58 | gum |

TABLE I-continued

| Compound No. | R[1] | R[2] | A | Olefinic[+] | Melting Point °C. |
|---|---|---|---|---|---|
| 803 | 4-C$_2$F$_5$-5-CH$_3$-pyrimidin-2-yl | CH$_3$ | H | 7.60 | 115–116 |
| 804 | 4-C$_2$H$_5$-pyrimidin-2-yl | CH$_3$ | H | 7.59 | 94–96 |
| 805 | Quinolin-2-yl-CH$_2$ | CH$_3$ | H | 7.59 | gum |
| 807 | 4,6-di-CH$_3$O-pyrimidin-2-yl-CH$_2$ | CH$_3$ | H | 7.56 | gum |
| 808 | 3-CF$_3$—C$_6$H$_4$—CH$_2$— | CH$_3$ | H | 7.58 | oil |
| 809 | 4-CH$_3$O—C$_6$H$_4$—CH$_2$— | CH$_3$ | H | 7.58 | gum |
| 810 | 2-F—C$_6$H$_4$—CH$_2$— | CH$_3$ | H | 7.58 | gum |
| 811 | 2-CH$_3$O—C$_6$H$_4$—CH$_2$— | CH$_3$ | H | 7.57 | gum |
| 812 | 4-F—C$_6$H$_4$—CH$_2$ | CH$_3$ | H | 7.58 | gum |
| 813 | 2-CH$_3$CHOH-pyrid-4-yl | CH$_3$ | H | 7.60 | gum |
| 814 | 2-CH$_3$CHF-pyrid-4-yl | CH$_3$ | H | 7.60 | gum |
| 815 | 4-CH$_3$CH$_2$CH$_2$-5-Cl-pyrimidin-2-yl | CH$_3$ | H | 7.60 | 103–104 |
| 816 | 2-Cl-4-CF$_3$-pyrimidin-5-yl | CH$_3$ | H | 7.59 | gum |
| 817 | 6-CH$_3$CHF-pyrimidin-4-yl | CH$_3$ | H | 7.61 | gum |
| 818 | 4-CF$_2$Cl-pyrimindin-2-yl | CH$_3$ | H | 7.60 | 80–81 |
| 819 | 4-CF$_2$Cl-5-CH$_3$-pyrimidin-2-yl | CH$_3$ | H | 7.60 | 110–111 |
| 820 | 4-CF$_3$-5-CO$_2$CH$_3$-pyrimidin-2-yl | CH$_3$ | H | 7.53 | oil |
| 821 | 2-CH$_3$CF$_2$-pyrid-4-yl | CH$_3$ | H | 7.60 | gum |
| 822 | 4-(CH$_3$)$_2$C=CH-pyrimidin-2-yl | CH$_3$ | H | 7.58 | oil |
| 823 | 4-CH$_3$CF$_2$-pyrid-2-yl | CH$_3$ | H | 7.61 | oil |
| 824 | 4-CF$_3$(CF$_2$)$_2$-5-CH$_3$-pyrimidin-2-yl | CH$_3$ | H | 7.60 | 100–101 |
| 825 | 4-CH$_3$CH=CH-pyrimidin-2-yl | CH$_3$ | H | | |
| 826 | 4-C$_2$F$_5$-6-CH$_3$-pyrimidin-2-yl | CH$_3$ | H | | |
| 827 | 4-[C$_2$H$_5$OC(CH$_3$)$_2$]-pyrimidin-2-yl | CH$_3$ | H | | |
| 828 | 4-CF$_3$-5-CH$_3$O-pyrimidin-2-yl | CH$_3$ | H | 7.58 | 148–149 |
| 829 | 4-CF$_3$-5-C$_2$H$_5$O-pyrimidin-2-yl | CH$_3$ | H | 7.58 | 136–137 |
| 830 | 4-(CH$_3$)$_3$C-5-CO$_2$CH$_3$-pyrimidin-2-yl | CH$_3$ | | | |
| 831 | 4-(CH$_3$)$_3$C-5-CO$_2$C$_2$H$_5$-pyrimidin-2-yl | CH$_3$ | H | | |
| 832 | 4-(CH$_3$)$_3$C-5-CONH$_2$-pyrimidin-2-yl | CH$_3$ | H | | |
| 833 | 4-(CH$_3$)$_3$C-5-cyano-pyrimidin-2-yl | CH$_3$ | H | | |
| 834 | 4-C$_2$H$_5$-5-CO$_2$CH$_3$-pyrimidin-2-yl | CH$_3$ | H | | |
| 835 | 4-C$_2$H$_5$-5-CO$_2$C$_2$H$_5$-pyrimidin-2-yl | CH$_3$ | H | | |
| 836 | 4-C$_2$H$_5$-5-CONH$_2$-pyrimidin-2-yl | CH$_3$ | H | | |
| 837 | 4-C$_2$H$_5$-5-cyano-pyrimidin-2-yl | CH$_3$ | H | | |
| 838 | 4-CH$_3$OCH$_2$CH$_2$-5-CO$_2$CH$_3$-pyrimidin-2-yl | CH$_3$ | H | | |
| 839 | 4-CH$_3$OCH$_2$CH$_2$-pyrimidin-2-yl | CH$_3$ | H | | |
| 840 | 4-allyloxy-5-CH$_3$-pyrimidin-2-yl | CH$_3$ | H | | |
| 841 | 4-propargyloxy-5-CH$_3$-pyrimidin-2-yl | CH$_3$ | H | | |
| 842 | 4-(CH$_3$)$_2$CF-pyrid-2-yl | CH$_3$ | H | | |
| 843 | 4-CH$_3$CHF-pyrid-2-yl | CH$_3$ | H | | |
| 844 | 4-CH$_2$=CF-pyrid-2-yl | CH$_3$ | H | | |
| 845 | 4,5-dichloro-pyrimidin-2-yl | CH$_3$ | H | | |
| 846 | 4-C$_2$H$_5$S-5-Cl-pyrimidin-2-yl | CH$_3$ | H | | |
| 847 | 4-HF$_2$CO-5-Cl-pyrimidin-2-yl | CH$_3$ | H | | |
| 848 | 4-C$_2$H$_5$S-5-CH$_3$-pyrimidin-2-yl | CH$_3$ | H | | |
| 849 | 4-HF$_2$CO-5-CH$_3$-pyrimidin-2-yl | CH$_3$ | H | | |
| 850 | 4-cyano-5-CH$_3$-pyrimidin-2-yl | CH$_3$ | H | | |
| 851 | 4-Cl-5-CH$_3$-pyrimidin-2-yl | CH$_3$ | H | | |
| 852 | 4-SF$_5$-pyrimidin-2-yl | CH$_3$ | H | | |
| 853 | 4-C$_2$F$_5$-5,6-CH$_3$-pyrimidin-2-yl | CH$_3$ | H | | |
| 854 | 4-C$_2$F$_5$-5-F-6-CH$_3$-pyrimidin-2-yl | CH$_3$ | H | | |
| 855 | 4-C$_2$F$_5$-5-F-pyrimidin-2-yl | CH$_3$ | H | | |
| 856 | 4-CF$_3$-5-F-6-CH$_3$-pyrimidin-2-yl | CH$_3$ | H | | |
| 857 | 4-CF$_3$-5-F-pyrimidin-2-yl | CH$_3$ | H | | |
| 858 | 4-CF$_3$-5-cyano-pyrimidin-2-yl | CH$_3$ | H | | |
| 859 | 4,6-di-CF$_3$-pyrimidin-2-yl | CH$_3$ | H | | |
| 860 | 4-CF$_3$-5-CONH$_2$-pyrimidin-2-yl | CH$_3$ | H | | |
| 861 | 4,5-(OCF$_2$O)-pyrimidin-2-yl | CH$_3$ | H | | |
| 862 | 4-CH(CH$_3$)$_2$-5-Cl-pyrimidin-2-yl | CH$_3$ | H | | |
| 863 | 4-CH$_3$CH$_2$CF$_2$-pyrimidin-2-yl | CH$_3$ | H | | |
| 864 | 4-C$_2$H$_5$-5-Cl-pyrimidin-2-yl | CH$_3$ | H | | |
| 865 | 4-SCN-pyrimidin-2-yl | CH$_3$ | H | | |
| 866 | 4-cyano-5-CH$_3$-pyrimidin-2-yl | CH$_3$ | H | | |
| 867 | 4,5-(OCH$_2$CH$_2$)-pyrimidin-2-yl | CH$_3$ | H | | |
| 868 | 5-cyano-pyrimidin-2-yl | CH$_3$ | H | | |
| 869 | 4-Cl-5-CH$_3$-pyrimidin-2-yl | CH$_3$ | H | | |
| 870 | 2-CF$_3$-pyrid-5-yl | CH$_3$ | H | | |
| 871 | 2-CF$_3$-pyrid-3-yl | CH$_3$ | H | | |
| 872 | 4-CF$_3$-pyrid-3-yl | CH$_3$ | H | | |
| 873 | 3-CF$_3$-pyrid-4-yl | CH$_3$ | H | | |
| 874 | 2-CF$_3$-pyrid-4-yl | CH$_3$ | H | | |

TABLE I-continued

| Compound No. | R¹ | R² | A | Olefinic⁺ | Melting Point °C. |
|---|---|---|---|---|---|
| 875 | 4-C₂F₅-pyrid-2-yl | CH₃ | H | | |
| 876 | 4-CH₂F-pyrid-2-yl | CH₃ | H | | |
| 877 | 4-CHF₂-pyrid-2-yl | CH₃ | H | | |
| 878 | 2-CH₂F-pyrid-4-yl | CH₃ | H | | |
| 879 | 2-CHF₂-pyrid-4-yl | CH₃ | H | | |
| 880 | 5-F-6-(CH₃)₂CHO-pyrimidin-4-yl | CH₃ | H | | |
| 881 | 4-(CH₃)₃C-pyrid-2-yl | CH₃ | H | 7.60 | gum |
| 882 | 5-F-isoquinolin-3-yl | CH₃ | H | | |
| 883 | 5-Cl-isoquinolin-3-yl | CH₃ | H | | |
| 884 | 5-CN-isoquinolin-3-yl | CH₃ | H | | |
| 885 | 5-NO₂-isoquinolin-3-yl | CH₃ | H | | |

⁺Chemical shift of singlet from olefinic proton on β-methoxypropenoate group of major oxime ether isomer (ppm from tetramethylsilane).
*The R¹ and R² groups combine to make the moiety listed under R¹.
φ See CHEMICAL FORMULAE pages for structure.

The compounds of the invention are characterized by the melting points given in Table I and/or by the NMR data given in Table II.

TABLE II

SELECTED PROTON NMR DATA

Table II shows selected proton NMR data for certain compounds described in Table I. Chemical shifts are measured in ppm from tetramethylsilane, and deuterochloroform was used as solvent throughout. The operating frequency of the NMR spectrometer was 270 MHz. The following abbreviations are used:

| s = singlet | sept = septet |
| d = doublet | m = multiplet |
| d = double doublet | br = broad |
| t = triplet | ppm = parts per million |
| q = quartet | |

| Compound No. | Proton NMR Data (δ) |
|---|---|
| 694 | 0.80(3H,t); 1.46(2H,sextuplet); 2.25(3H,s); 2.60(2H,m); 3.68(3H,s); 3.81(3H,s); 3.99(3H,s); 5.13(2H,s); 7.16(1H,m); 7.33(2H,m); 7.47(1H,m); 7.58(1H,s); 8.62(1H,s) ppm. |
| 695 | 1.80–2.01(4H,m); 2.06–2.19(2H,m); 2.36(3H,s); 2.79–2.86(1H,m); 3.78(3H,s); 3.82(3H,s); 4.38(2H,d); 5.32(2H,s); 6.66(1H,d); 7.15–7.20(1H,m); 7.30–7.39(2H,m); 7.53–7.59(1H,m); 7.59(1H,s); 8.50(1H,d) ppm. |
| 697 | 2.31(3H,s); 3.68(3H,s); 3.81(3H,s); 3.87(3H,s); 5.16(2H,s); 7.15(2H,m); 7.33(2H,s); 7.53(1H,m); 7.59(1H,s) 7.83(1H,d); 8.26(1H,d); ppm. |
| 698 | 2.26(3H,s); 3.69(3H,s); 3.83(3H,s); 4.89(2H,d); 5.19(2H,s); 5.29(1H,d); 5.40(1H,d); 6.06(1H,8 lines); 7.18(1H,m); 7.20(1H,m); 7.34(2H,m); 7.49(1H,m); 7.60(1H,s); 8.75(1H,s) ppm. |
| 699 | 2.30(3H,s); 2.37(3H,q); 3.68(3H,s); 3.83(3H,s); 5.16(2H,s); 7.18(1H,m); 7.34(2H,m); 7.46(1H,m); 7.60(1H,s); 9.14(1H,s) ppm. |
| 700 | 0.88(3H,t); 1.43(2H,m); 2.27(6H,s); 2.82(2H,m); 3.68(3H,s); 3.81(3H,s); 5.14(2H,s); 7.16(1H,m); 7.33(2H,m); 7.46(1H,m); 7.59(1H,s); 7.70(1H,br); 9.04(1H,s) ppm. |
| 701 | 0.80(3H,t); 1.45(2H,m); 2.20(3H,s); 2.30(3H,s); 2.67(2H,m); 3.68(3H,s); 3.81(3H,s); 5.16(2H,s); 7.17(1H,m); 7.33(2H,m); 7.46(1H,m); 7.59(1H,s); 9.09(1H,s) ppm. |
| 702 | 1.76(3H,s); 3.45(2H,s); 3.68(3H,s); 3.81(3H,s); 5.05(2H,s); 7.10–7.19(3H,m); 7.29–7.36(2H,m); 7.40–7.48(1H,m); 7.58(1H,s); 8.51(2H,t) ppm. |
| 705 | 1.73(3H,s); 3.70(3H,s); 3.83(3H,s); 5.05(2H,s); 5.07(2H,s); 7.15–7.20(1H,m); 7.31–7.38(2H,m); 7.39–7.44(1H,m); 7.59(1H,s); 7.95(1H,s); 8.07(1H,s) ppm. |
| 708 | 1.20(3H,t); 2.05(2H,m); 2.33(3H,s); 2.50(2H,q); 3.57(2H,t); 3.68(3H,s); 3.82(3H,s); 4.52(2H,t); 5.32(2H,s); 6.68(1H,d); 7.0–7.9(4H,m); 7.58(1H,s); 8.52(1H,d) ppm. |
| 709 | 2.20(3H,s); 3.35(3H,s); 3.68(3H,s); 3.82(3H,s); 5.14(2H,s); 6.41(1H,d); 7.1–7.6(4H,m); 7.86(1H,d) ppm. |

TABLE II-continued

SELECTED PROTON NMR DATA

| 710 | 2.37(3H,s); 3.68(3H,s); 3.82(3H,s); 4.09(2H,m); 5.32(2H,s); 7.1–7.6(4H,m); 7.17(1H,d); 7.58(1H,s); 8.53(1H,d) ppm. |
| 711 | 2.37(3H,s); 3.68(3H,s); 3.82(3H,s); 5.33(2H,s); 7.1–7.6(4H,m); 7.31(1H,d); 7.58(1H,s); 8.68(1H,d) ppm. |
| 712 | 1.80(3H,s); 2.72(2H,t); 3.79(3H,s); 3.82(3H,s); 4.34(2H,t); 4.99(2H,s); 6.14–6.17(1H,m); 7.12–7.19(1H,m); 7.26–7.60(5H,m); 7.59(1H,s) ppm. |
| 713 | 2.26(3H,s); 2.50(1H,t); 3.70(3H,s); 3.84(3H,s); 5.03(2H,d); 5.19(2H,s); 7.18(1H,m); 7.26(1H,s); 7.34(2H,m); 7.48(1H,m); 7.60(1H,s); 8.80(1H,s) ppm. |
| 715 | 0.83(3H,t); 1.48(2H,m); 2.24(3H,s); 2.46(1H,t); 2.64(2H,m); 3.67(3H,s); 3.81(3H,s); 5.03(2H,d); 5.14(2H,s); 7.17(1H,m); 7.33(2H,m); 7.46(1H,m); 7.58(1H,s); 8.64(1H,s) ppm. |
| 718 | 2.54(6H,s); 3.69(3H,s); 3.81(3H,s); 5.20(2H,s); 5.67(2H,brs); 7.02(1H,s); 7.10–7.60(4H,m); 7.56(1H,s) ppm. |
| 719 | 2.56(6H,s); 3.69(3H,s); 3.82(3H,s); 5.40(2H,s); 7.06(1H,s); 7.10–7.60(4H,m); 7.59(1H,s) ppm. |
| 720 | 2.16(3H,s); 2.55(6H,s); 3.67(3H,s); 3.80(3H,s); 5.25(2H,s); 7.04(1H,s); 7.10–7.60(4H,m); 7.55(1H,s) ppm. |
| 722 | 1.79(3H,s); 3.70(3H,s); 3.83(3H,s); 4.84(2H,s); 5.03(2H,s); 6.14(1H,dd); 6.59(1H,d); 7.13–7.20(2H,m); 7.26–7.38(3H,m); 7.39–7.46(1H,m); 7.59(1H,s) ppm. |
| 731 | 1.52–1.72(6H,m); 2.15–2.23(2H,m); 2.44–2.53(2H,t); 3.68(3H,s); 3.81(3H,s); 4.97(2H,s); 7.11–7.18(1H,m); 7.25–7.36(2H,m); 7.43–7.50(1H,m); 7.56(1H,s) ppm. |
| 737 | 2.43(3H,s); 3.63(3H,s); 3.77(3H,s); 5.23(2H,s); 7.22(1H,m); 7.37(2H,m); 7.44(1H,m); 7.54(1H,t); 7.60(1H,s); 7.77(1H,t); 8.20(1H,d); 8.39(1H,d); 8.58(1H,s) ppm. |
| 739 | 1.68–1.79(4H,m); 2.30–2.46(4H,m); 3.76(3H,s); 3.80(3H,s); 4.98(2H,s); 7.10–7.15(1H,m); 7.23–7.35(2H,m); 7.43–7.48(1H,m); 7.55(1H,s) ppm. |
| 740 | 2.25(3H,s); 3.68(3H,s); 3.82(3H,s); 4.88(2H,q); 5.19(2H,s); 7.16(1H,m); 7.35(2H,m); 7.50(1H,m); 7.58(1H,s); 8.63(1H,s) ppm. |
| 743 | 0.67(3H,t); 1.38(2H,m); 2.25(6H,s); 2.86(2H,m); 3.67(6H,s); 3.79(6H,s); 5.13(4H,s); 7.16(2H,m); 7.32(2H,m); 7.46(2H,m); 7.58(2H,s); 9.02(1H,s) ppm. |
| 744 | 2.30(6H,s); 3.69(6H,s); 3.80(6H,s); 5.25(4H,s); 7.18(2H,m); 7.35(4H,m); 7.50(2H,m); 7.60(2H,s); 9.17(1H,s) ppm. |
| 746 | 2.41(3H,s); 3.68(3H,s); 3.82(3H,s); 5.32(2H,s); 5.73(1H,d); 6.53(1H,d); 6.79(1H,m); 7.18(1H,m); 7.22(1H,d); 7.34(2H,m); 7.54(1H,m); 7.58(1H,s); 8.78(1H,d). |
| 747 | 1.32(3H,t); 2.27(3H,s); 2.99(2H,q); 3.68(3H,s); 3.81(3H,s); 5.20(2H,s); 7.17(1H,m); 7.33(2H,m); 7.52(1H,m); 7.58(1H,s); 8.98(1H,s) ppm. |
| 751 | 1.99(2H,dd); 2.40(3H,s); 3.68(3H,s); 3.82(3H,s); 5.31(2H,s); 6.47(1H,d); 7.10(1H,d); 7.16(3H,m); 7.34(2H,m); 7.55(1H,m); 7.59(1H,s); 8.68(1H,d) ppm. |
| 761 | 2.46(3H,s); 2.73(3H,s); 3.70(3H,s); 3.84(3H,s); 5.24(2H,s); 7.09(1H,s); 7.20(1H,m); 7.36(2H,m); 7.49(1H,m); 7.61(1H,s); 8.45(1H,s) ppm. |
| 762 | 2.09(3H,s); 2.51(3H,s); 3.68(3H,s); 3.81(3H,s); 3.93(6H,s); |

TABLE II-continued

SELECTED PROTON NMR DATA

| | |
|---|---|
| | 5.13(2H,s); 7.1–7.6(4H,m); 7.57(1H,s) ppm. |
| 764 | 2.15(2H,m); 2.41(3H,s); 2.96(2H,m); 3.06(2H,m); 5.34(2H,s); 7.1–7.6(4H,m); 7.57(1H,s); 8.58(1H,s) ppm. |
| 765 | 1.37(9H,s); 2.30(3H,s); 3.69(3H,s); 3.82(3H,s); 5.23(2H,s); 7.18(1H,m); 7.35(2H,m); 7.50(1H,m); 7.60(1H,s); 7.84(1H,s); 9.14(1H,s) ppm. |
| 769 | 2.21(3H,s); 3.68(3H,s); 3.81(3H,s); 5.13(2H,s); 5.95(2H,s); 6.76–6.81(1H,d); 7.06–7.11(1H,dd); 7.14–7.23(2H,m); 7.25–7.38(2H,m); 7.50–7.55(1H,m); 7.60(1H,s) ppm. |
| 770 | 2.21(3H,s); 3.68(3H,s); 3.81(3H,s); 3.89(3H,s); 3.91(3H,s); 5.14(2H,s); 6.83(1H,d); 7.10–7.18(2H,m); 7.24–7.38(3H,m); 7.50–7.56(1H,m); 7.58(1H,s) ppm. |
| 772 | 1.27(6H,dd); 2.16(3H,s); 2.64(3H,s); 3.10 (1H,sept); 3.64(3H,s); 3.76(3H,s); 4.98(2H,q); 7.09(1H,m); 7.26(3H,m); 7.53(1H,s); 8.94(1H,s) ppm. |
| 773 | 3.68(3H,s); 3.82(3H,s); 5.22(2H,s); 6.91, 7.10, 7.30(1H,t); 7.15–8.35(8H,m); 7.60(1H,s) ppm. |
| 776 | 3.68(3H,s); 3.80(3H,s); 3.82(3H,s); 5.20(2H,s); 6.89, 7.09, 7.29(1H,t); 6.98(1H,m); 7.1–7.5(7H,m); 7.60(1H,s) ppm. |
| 779 | 1.45(3H,t); 2.31(3H,s); 2.64(3H,s); 3.69(3H,s); 3.82(3H,s); 4.52(2H,q); 5.34(2H,s); 7.13–7.21(1H,m); 7.29–7.40(2H,m); 7.47–7.56(1H,m) ppm. |
| 780 | 2.18(3H,s); 2.99(2H,br); 3.21(2H,t); 3.60(2H,br); 3.65(3H,s); 3.78(3H,s); 5.00(2H,s); 7.12(1H,m); 7.27(3H,m); 7.54(1H,s); 9.00(1H,s) ppm. |
| 784 | 2.38(3H,s); 3.68(3H,s); 3.82(3H,s); 5.20(2H,s); 6.89, 7.10, 7.30(1H,t); 7.1–7.5(8H,m); 7.60(1H,s) ppm. |
| 788 | 1.37(6H,d); 3.70(3H,s); 3.83(3H,s); 5.29(2H,s); 5.44(1H,m); 6.60(1H,d); 7.10–7.60(4H,m); 7.59(1H,s); 8.10(1H,s); 8.46(1H,d) ppm. |
| 789 | 2.34(3H,s); 3.67(3H,s); 3.81(3H,s); 5.32(2H,s); 7.1–7.6(4H,m); 7.58(1H,s); 8.96(1H,s) ppm. |
| 794 | 3.70(3H,s); 3.81(3H,s); 5.27(2H,s); 7.21(1H,m); 7.36(2H,m); 7.56(1H,m); 7.60(1H,t); 7.61(1H,d); 7.63(1H,s); 7.76(1H,t); 8.14(1H,d); 8.40(1H,d); 8.70(1H,s); 8.91(1H,d) ppm. |
| 795 | 2.34(3H,s); 3.70(3H,s); 3.84(3H,s); 5.22(2H,s); 7.17(1H,m); 7.34(2H,m); 7.43(1H,dd); 7.51(1H,m); 7.61(1H,s); 8.12(1H,s); 8.42(1H,d) ppm. |
| 797 | 2.37(3H,s); 3.65(3H,s); 3.77(3H,s); 5.22(2H,s); 7.21(1H,m); 7.32(1H,d); 7.36(2H,m); 7.50(1H,t); 7.54(1H,m); 7.60(1H,s); 7.70(1H,t); 8.01(1H,d); 8.11(1H,d); 8.90(1H,d) ppm. |
| 800 | 1.55(6H,s); 2.38(3H,s); 3.22(3H,s); 3.68(3H,s); 3.82(3H,s); 5.34(2H,s); 7.1–7.6(4H,m); 7.59(1H,s); 8.79(1H,d) ppm. |
| 802 | 2.38(3H,s); 3.68(3H,s); 3.82(3H,s); 5.34(2H,s); 7.0–7.9(4H,m); 7.58(1H,s); 8.95(1H,s) ppm. |
| 805 | 1.77(3H,s); 3.62(3H,s); 3.76(3H,s); 3.92(2H,s); 5.07(2H,s); 7.1–7.8(8H,m); 7.59(1H,s); 8.11(1H,m); 8.84(1H,m) ppm. |
| 807 | 2.51(3H,s); 3.68(3H,s); 3.81(3H,s); 3.93(6H,s); 4.05(2H,m); 5.13(2H,s); 7.1–7.6(4H,s); 7.57(1H,s); 7.60(1H,s) ppm. |
| 808 | 1.76(3H,s); 3.51(2H,s); 3.65(3H,s); 3.80(3H,s); 5.05(2H,s); 7.1–7.6(8H,m); 7.58(1H,s) ppm. |
| 809 | 1.74(3H,s); 3.39(2H,s); 3.67(3H,s); 3.79(3H,s); 3.81(3H,s); 5.05(2H,s); 6.82(2H,d); 7.10(2H,d); 7.12(1H,m); 7.30(2H,m); 7.48(1H,m); 7.58(1H,s) ppm. |
| 810 | 1.79(3H,s); 3.51(2H,s); 3.68(3H,s); 3.82(3H,s); 5.04(2H,s); 7.0–7.35(7H,m); 7.48(1H,m); 7.58(1H,s) ppm. |
| 811 | 1.78(3H,s); 3.50(2H,s); 3.67(3H,s); 3.79(3H,s); 3.82(3H,s); 5.04(2H,s); 6.88(2H,m); 7.1–7.4(5H,m); 7.49(1H,m); 7.57(1H,s) ppm. |
| 812 | 1.73(3H,s); 3.40(2H,s); 3.65(3H,s); 3.80(3H,s); 5.03(2H,s); 6.95(2H,m); 7.13(3H,m); 7.29(2H,m); 7.45(1H,m); 7.57(1H,s) ppm. |
| 813 | 1.52(3H,d); 2.21(3H,s); 3.67(3H,s); 3.81(3H,s); 4.91(1H,m); 5.19(2H,s); 7.1–7.6(4H,m); 7.60(1H,s); 8.50(1H,d) ppm. |
| 814 | 1.65(3H,dd); 2.23(3H,s); 3.70(3H,s); 3.82(3H,s); 5.20(2H,s); 5.61(1H,q); 7.1–7.6(4H,m); 7.60(1H,s); 7.70(1H,s); 8.53(1H,d) ppm. |
| 816 | 2.19(3H,s); 3.68(3H,s); 3.82(3H,s); 5.15(2H,s); 7.1–7.5(4H,m); 7.59(1H,s); 8.72(1H,s) ppm. |
| 817 | 1.70(3H,dd); 2.30(3H,s); 3.70(3H,s); 3.84(3H,s); 5.23(2H,s); 7.1–7.6(4H,m); 7.61(1H,s); 8.01(1H,s); 9.13(1H,s) ppm. |
| 820 | 1.36(3H,t); 2.36(3H,s); 3.63(3H,s); 3.77(3H,s); 4.41(2H,q); 5.32(2H,s); 7.0–7.5(4H,m); 7.53(1H,s); 9.22(1H,s) ppm. |
| 821 | 2.02(3H,t); 2.23(3H,s); 3.69(3H,s); 3.83(3H,s); 5.20(2H,s); 7.1–7.6(4H,m); 7.88(1H,s); 7.59(1H,d); 8.62(1H,d) ppm. |
| 822 | 2.01(3H,s); 2.26(3H,s); 2.40(3H,s); 3.68(3H,s); 3.82(3H,s); 5.33(2H,s); 6.25(1H,s); 7.00(1H,d); 7.1–7.6(4H,m); 7.58(1H,s); 8.68(1H,d) ppm. |
| 823 | 1.93(3H,t); 2.35(3H,s); 3.69(3H,s); 3.82(3H,s); 5.22(2H,s); 7.1–7.6(5H,m); 7.61(1H,s); 8.01(1H,m); 8.66(1H,d) ppm. |
| 881 | 1.33(9H,s); 2.33(3H,s); 3.69(3H,s); 3.82(3H,s); 5.20(2H,s); 7.17(1H,m); 7.24(1H,dd); 7.33(2H,m); 7.55(1H,m); 7.60(1H,s); 7.87(1H,d); 8.49(1H,d) ppm. |

The compounds of the invention of formula (I) can be prepared by the steps shown in Scheme 1. Throughout Scheme 1 the terms A, $R^1$ and $R^2$ are as defined above. $R^*$ is either $R^1$ or $R^2$ and X is a leaving group (such as halogen (chlorine, bromine or iodine) or $OSO_2CF_3$).

A compound of formula (I) can be prepared by treating an oxime of formula (III) with a suitable base (such as sodium hydride or sodium N,N-dimethylformamide or methoxide), in a suitable solvent (such as tetrahydrofuran), to form the anion and then adding a compound of formula (II). Oximes of formula (III) are known in the chemical literature. The compound of formula (II) where X is bromine and the propenoate group has the (E)-configuration is described in EP-A-0203606.

An oxime of formula (III) can be prepared by reacting a compound of formula (XI) with hydroxylamine in a suitable solvent (for example a mixture of a primary alcohol (such as methanol or ethanol) with water) optionally in the presence of a buffer (such as a salt of an organic acid (for example sodium acetate)).

A compound of formula (XI) can be prepared by treating a compound of formula (XII) (R* is either $R^1$ or $R^2$ but is not methyl) with an acid, preferably a strong mineral acid such as hydrochloric acid of suitable concentration, in a suitable solvent, for example acetone. A compound of formula (XII) can be prepared by treating a compound of formula (XIII) (wherein X is typically chlorine, bromine or $OSO_2CF_3$) with an alkoxyvinyl tin compound (for example (1-ethoxyvinyl)tri-n-butyltin) in the presence of a suitable catalyst (such as bis(triphenylphosphine)palladium(II) chloride) in a suitable solvent (for example N,N-dimethylformamide).

Alternatively, a compound of formula (XI) can be prepared by reacting a compound of formula (XIV) with a methyl magnesium halide in a suitable solvent (for example diethyl ether or tetrahydrofuran). A compound of formula (XIV) can be prepared by reacting a compound of formula (XIII) with a trialkylamine (such as trimethylamine) which is preferably in aqueous solution, and in the presence of a suitable organic solvent (for example diethyl ether), and then introducing a source of cyanide anions (for example potassium or sodium cyanide).

Alternatively, compounds of formulae (XI), (XII), (XIII) and (XIV) can be prepared by methods known in the literature.

Alternatively, a compound of formula (I) can be prepared by treating a substituted hydroxylamine of formula (XV) (or a salt thereof, for example its hydrochloride salt) with a compound of formula (XI). The substituted hydroxylamine (XV) wherein A is hydrogen can be prepared as described in EP-A-0463488.

Alternatively, a compound of formula (I) can be prepared from a phenylacetate of formula (VI) or from a ketoester of formula (X) by the steps shown in Scheme 2. Throughout Scheme 2 the terms A, $R^1$, $R^2$ and X are as defined above, $R^5$ is hydrogen or a metal (such as sodium or potassium), and R is an alkyl group. Each transformation is performed at a suitable temperature and usually, though not always, in a suitable solvent.

Thus, a compound of formula (I) can be prepared by treatment of a phenylacetate of formula (VI) with a base (such as sodium hydride or sodium methoxide) and methyl formate. If a species of formula $CH_3L$, wherein L is a leaving group such as a halide (for example chlorine, bromine or iodine), or a $CH_3SO_4$ anion, is then added to the reaction mixture, a compound of formula (I) is obtained. If a protic acid is added to the reaction mixture, a compound of formula (IX), wherein $R^5$ is hydrogen, is obtained. Alternatively, the compound of formula (IX) wherein $R^5$ is a metal (such as sodium), can be isolated from the reaction mixture.

A compound of formula (IX) wherein $R^5$ is a metal can be converted into a compound of formula (I) by treatment with a species $CH_3L$, wherein L is as defined above. A compound of formula (IX) wherein $R^5$ is hydrogen can be converted into a compound of formula (I) by successive treatment with a base (such as potassium carbonate) and a species of general formula $CH_3L$.

Alternatively, a compound of formula (I) can be prepared from an acetal of formula (IV) by elimination of methanol under either acidic or basic conditions. Examples of reagents or reagent mixtures which can be used for this transformation are lithium di-isopropylamide; potassium hydrogen sulphate (see, for example, T. Yamada, H. Hagiwara and H. Uda, *J. Chem. Soc. Chemical Communications*, 1980, 838, and references therein); and triethylamine, often in the presence of a Lewis acid such as titanium tetrachloride (see, for example, K. Nsunda and L. Heresi, *J. Chem. Soc. Chemical Communications*, 1985, 1000).

An acetal of formula (IV) can be prepared by treatment of a methyl silyl ketene acetal of formula (V) with trimethyl orthoformate in the presence of a Lewis acid such as titanium tetrachloride (see, for example, K. Saigo, M. Osaki and T. Mukaiyama, *Chemistry Letters*, 1976, 769).

A methyl silyl ketene acetal of formula (V) can be prepared by treating a phenylacetate of formula (VI) with a base and a trialkyisilyl halide of formula $R_3SiCl$ or $R_3SiBr$, such as trimethylsilyl chloride, or a base (such as triethylamine) and a trialkylsilyl triflate of formula $R_3Si-OSO_2CF_3$ (see, for example, C. Ainsworth, F. Chen and Y. Kuo, *J. Organometallic Chemistry*, 1972, 46, 59).

It is not always necessary to isolate the intermediates (IV) and (V); under appropriate conditions a compound of formula (I) can be prepared from a phenylacetate of formula (VI) in "one pot" by the successive addition of suitable reagents listed above.

A phenylacetate of formula (VI) can be prepared from a phenylacetate of formula (VII). Thus, if an oxime of general formula (III) is treated with a suitable base (such as sodium hydride or sodium methoxide) and a phenyl acetate of formula (VII) added, a phenylacetate of formula (VI) is obtained.

A phenylacetate of formula (VII) can be prepared by treating an isochromanones of formula (VIII) with HX (wherein X is preferably bromine) in methanol. This transformation can also be accomplished in 2 steps if the isochromanone of formula (VIII) is treated with HX in a non-alcoholic solvent, and the resulting phenylacetic acid is then esterified using standard procedures (see, for example, I. Matsumoto and J. Yoshizawa, Jpn. Kokai (Tokkyo Koho) 79 138 536, 27.10.1979, *Chem. Abs.*, 1980, 92, 180829h; and G. M. F. Lim, Y. G. Perron and R. D. Droghini, *Res. Discl.*, 1979, 188, 672, *Chem. Abs.*, 1980, 92, 128526t). Isochromanones of formula (VIII) are well known in the chemical literature.

Alternatively, a compound of formula (I) can be prepared by treatment of a ketoester of formula (XI) with a methoxymethylenation reagent such as methoxymethylenetriphenylphosphorane (see, for example, W. Steglich, G. Schramm, T. Anke and F. Oberwinkler, EP-A-0044448, published 4 Jul. 1980).

A ketoester of formula (XI) can be prepared from a ketoester of formula (X), by treatment with the anion of an oxime of formula (III) as described above. Ketoesters of formula (X) are described in EP-A-0331061.

Therefore, to summarise, Schemes 1 and 2 illustrate certain methods by which the oxime ether and the 3-methoxypropenoate moieties, respectively, may be constructed in the final stages of the synthesis of the compounds of the invention of formula (I). An alternative final stage or stages in the synthesis of the compounds of the invention of formula (I) is a modification to one of the groups $R^1$ or $R^2$ or to the substituent A. Thus, for example, if A, or a substituent on one of the groups $R^1$ and $R^2$ when that group is a pyridine or pyrimidine ring, is a suitably positioned amino group, it may be converted in the final stages of the reaction sequence through diazotisation into a halogen atom.

In a further aspect the present invention provides a process for the preparation of a compound of formula (I).

The compounds of formula (I) are active fungicides and may be used to control one or more of the following pathogens: *Pyricularia oryzae* on rice and wheat and other Pyricularia spp. on other hosts; *Puccinia recondita, Puccinia striiformis* and other rusts on wheat, *Puccinia hordei, Puccinia striiformis* and other rusts on barley, and rusts on other hosts e.g. turf, rye, coffee, pears, apples, peanuts, sugar beet, vegetables and ornamental plants; *Erysiphe graminis* (powdery mildew) on barley, wheat, rye and turf and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines; Cochliobolus spp., Helminthosporium spp., Drechslera spp. (Pyrenophora spp.), Rhynchosporium spp., Septoria spp. (including *Mycosphaereila graminicola* and *Leptosphaeria nodorum*), *Pseudocercosporella herpotrichoides* and *Gaeumannomyces graminis* on cereals (e.g. wheat, barley, rye), turf and other hosts; *Cercospora arachidicola* and *Cercosporidium personarum* on peanuts and other Cercospora species on other hosts, for example, sugar beet, bananas, soya beans and rice; Botrytis cinerea (grey mould) on tomatoes, strawberries, vegetables, vines and other hosts and other Botrytis spp. on other hosts; Alternaria spp. on vegetables (e.g. cucumber), oil-seed rape, apples, tomatoes, cereals (e.g. wheat) and other hosts; Venturia spp. (including *Venturia inaequalis* (scab)) on apples, pears, stone fruit, tree nuts and other hosts; Cladosporium spp. on a range of hosts including cereals (e.g. wheat); Monilinia spp. on stone fruit, tree nuts and other hosts; Didymella spp. on tomatoes, turf, wheat and other hosts; Phoma spp. on oil-seed rape, turf, rice, potatoes, wheat and other hosts; Aspergillus spp. and Aureobasidium spp. on wheat, lumber and other hosts; Ascochyta spp. on peas, wheat, barley and other hosts; *Plasmopara viticola* on vines; other downy mildews such as *Bremia lactucae* on lettuce, Peronospora spp. on soybeans, tobacco, onions and other hosts, *Pseudoperonospora humuli* on hops and *Pseudoperonospora cubensis* on cucurbits; Pythium spp. on turf and other hosts; *Phytophthora infestans* on potatoes and tomatoes and other Phytophthora spp. on vegetables, strawberries, avocado, pepper, ornamentals, tobacco, cocoa and other hosts; *Thanatephorus cucumeris* on rice and turf and other Rhizoctonia species on various hosts such as wheat and barley, vegetables, cotton and turf; Sclerotinia spp. on turf, peanuts, oil-seed rape and other hosts; Sclerotium spp. on turf, peanuts and other hosts; Colletotrichum spp. on a range of hosts including turf, coffee and vegetables; *Laetisaria fuciformis* on turf; Mycosphaerella spp. on banana, peanut, citrus, pecan, papaya and other hosts; Diaporthe spp. on citrus, soybean, melon, pear, lupin and other hosts; Elsinoe spp. on citrus, vines, olives, pecans, roses and other hosts; Pyrenopeziza spp. on oil-seed rape and other hosts; *Oncobasidium theobromae* on cocoa causing vascular streak dieback; Fusarium spp., Typhula spp., *Microdochium nivale*, Ustilago spp., Urocystis spp., Tilletia spp., and *Claviceps purpurea* on a variety of hosts but particularly wheat, barley, turf and maize; Ramularia spp. on sugar beet and other hosts; post-harvest diseases particularly of fruit (e.g. *Pencillium digitatum* and *P. italicum* and *Trichoderma viride* on oranges, *Colletotrichum musae* and *Gloeosporium musarum* on bananas and *Botrytis cinerea* on grapes); other pathogens on vines, notably *Eutypa lata, Guignardia bidweilii, Phellinus igniarus, Phomopsis viticola, Pseudopezicula tracheiphila* and *Stereum hirsutum*; other pathogens on lumber, notably *Cephaloascus fragrans,* Ceratocystis spp., *Ophiostoma piceae*, Penicillium spp., *Trichoderma pseudokoningii, Trichoderma viride Trichoderma harzianum, Aspergillus niger, Leptographium lindbergi* and *Aureobasidium pullulans;* and fungal vectors of viral diseases e.g. *Polymyxa graminis* on cereals as the vector of barley yellow mosaic virus (BYMV).

Some of the compositions show a broad range of activities against fungi in vitro.

The compounds may move acropetally/locally in plant tissue. Moreover, the compounds may be volatile enough to be active in the vapour phase against fungi on the plant.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides fungicidal compositions comprising a compound as hereinbefore defined and an acceptable carrier or diluent therefor. It is preferred that all compositions, both solid and liquid formulations, comprise 0.0001 to 95%, more preferably 1 to 85%, for example 1 to 25% or 25 to 60%, of a compound as hereinbefore defined.

When applied the foliage of plants, the compounds of the invention are applied at rates of 0.1 g to 10 kg, preferably 1 g to 8 kg, more preferably 10 g to 4 kg, of active ingredient (invention compound) per hectare.

When used as seed dressings, the compounds of the invention are used at rates of 0.0001 g (for example 0.001 g or 0.05 g) to 10 g, preferably 0.005 g to 8 g, more preferably 0.005 g to 4 g, of active ingredient (invention compound) per kilogram of seed.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems.

The invention compounds may also be injected into plants or sprayed onto vegetation using electrodynamic spraying techniques or other low volume methods or applied by land or aerial irrigation systems.

The term "plant" as used herein includes seedlings, bushes and trees. Furthermore, the fungicidal method of the invention includes preventative, protectant, prophylactic, systemic and eradicant treatments.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or N,N-dimethylformamide). The compositions may also be in the form of water dispersible powders or water dispersible granules comprising wetting or dispersing agents to facilitate the dispersion in liquids. The powders and granules may also contain fillers and suspending agents.

The compositions may also be in the form of soluble powders or granules, or in the form of solutions in polar solvents.

Soluble powders may be prepared by mixing the active ingredient with a water-soluble salt such as sodium bicarbonate, sodium carbonate, magnesium sulphate or a polysaccharide, and a wetting or dispersing agent to improve water dispersibility/solubility. The mixture may then be ground to a fine powder. Similar compositions may also be granulated to form water-soluble granules. Solutions may be prepared by dissolving the active ingredient in polar solvents such as ketones, alcohols and glycol ethers. These solutions may contain surface active agents to improve water dilution and prevent crystallisation in a spray tank.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Aqueous suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the uptake, distribution, adhesive power and resistance to rain on treated surfaces, the different compositions can be better adapted for various utilities. Other additives may be included to improve the biological efficacy of the various formulations. Such additives can be surface active materials to improve the wetting and retention on surfaces treated with the formulation and also the uptake and mobility of the active material, or additionally can include oil based spray additives, for example, certain mineral oil and natural plant oil (such as soya bean and rape seed oil) additives, or blends of them with other adjuvants.

The invention compounds can be used as mixtures with fertilisers (e.g. nitrogen-, potassium- or phosphorus-containing fertilisers). Compositions comprising only granules of fertiliser incorporating, for example coated with, a compound of formula (I) are preferred. Such granules suitably contain up to 25% by weight of the compound. The invention therefore also provides a fertiliser composition comprising a fertiliser and the compound of general formula (I) or a salt or metal complex thereof.

Water dispersible powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and tri-isopropylnaphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, alkyl glucosides, polysaccharides and the lecithins and the condensation products of the said partial esters with ethylene oxide. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 1–85%, for example 1–25% or 25–60%, by weight of the active ingredient. After dilution to form aqueous preparations, such preparations may contain varying amounts of the active ingredient depending upon the intended purpose, but an aqueous preparation containing 0.0001 to 10%, for example 0.005 to 10%, by weight of active ingredient may be used.

The compositions of this invention may contain other compounds having biological activity, e.g. compounds having similar or complementary fungicidal activity or which possess plant growth regulating, herbicidal or insecticidal activity.

By including another fungicide, the resulting composition can have a broader spectrum of activity or a greater level of intrinsic activity than the compound of general formula (I) alone. Further the other fungicide can have a synergistic effect on the fungicidal activity of the compound of general formula (I). Examples of fungicidal compounds which may be included in the composition of the invention are (RS)-1-aminopropylphosphonic acid, (RS)-4-(4-chlorophenyl)-2-phenyl-2-)1H-1,2,4--triazol-1-ylmethyl) butyronitrile, (Z)-N-but-2-enyloxymethyl-2-chloro-2'.6'-diethylacetanilide, 1-(2-cyano-2-methoxyiminoacetyl)-3-ethyl urea, 4-(2,2-difluoro-1,3-benzodioxol-4-yl)pyrrole-3-carbonitrile, 4-bromo-2-cyano-N,N-dimethyl-6-trifluoromethylbenzimidazole-1-sulphonamide, 5-ethyl-5,8-dihydro-8-oxo(1,3)-dioxol-(4,5-g)quinoline-7-carboxylic acid, α-[N-(3-chloro-2,6-xylyl)-2-methoxyacetamido]-γ-butyrolactone, N-(2-methoxy-5-pyridyl)-cyclopropane carboxamide, alanycarb, aldimorph, ampropylfos, anilazine, azaconazole, BAS 490F, benalaxyl, benomyl, biloxazol, binapacryl, bitertanol, blasticidin S, bromuconazole, bupirimate, butenachlor, buthiobate, captafol, captan, carbendazim, carbendazim chlorhydrate, carboxin, chinomethionate, chlorbenzthiazone, chloroneb, chlorothalonil, chlorozolinate, clozylacon, copper containing compounds such as copper oxychloride, copper oxyquinolate, copper sulphate, copper tallate, and Bordeaux mixture, cycloheximide, cymoxanil, cyproconazole, cyprofuram, debacarb, di-2-pyridyl disulphide 1,1'-dioxide, dichlofluanid, dichlone, diclobutrazol, diclomezine, dicloran, didecyl dimethyl ammonium chloride, diethofencarb, difenoconazole, O,O-di-iso-propyl-5-benzyl thiophosphate, dimefluazole, dimetconazole, dimethomorph, dimethirimol, diniconazole, dinocap, dipyrithione, ditalimfos, dithianon, dodemorph, dodine, doguadine, edifenphos, epoxiconazole, etaconazole, ethirimol, ethoxyquin, ethyl (Z)-N-benzyl-N-([methyl (methyl-thioethylideneamino-oxycarbonyl)amino]thio)-β-alaninate, etridiazole, fenaminosulph, fenapanil, fenarimol, fenbuconazole, fenfuram, fenpiclonil, fenpropidin, fenpropimorph, fentin acetate, fentin hydroxide, ferbam, ferimzone, fluazinam, fludioxonil, fluoroimide, fluquinconazole, flusilazole, flutolanil, flutriafol, folpet, fuberidazole, furalaxyl, furconazole-cis, guazatine, hexaconazole, hydroxyisoxazole, hymexazole, ICIA5504, imazalil, imibenconazole, ipconazole, iprobenfos, iprodione, isopropanyl butyl carbamate, isoprothiolane, kasugamycin, mancozeb, maneb, mepanipyrim, mepronil, metalaxyl, metconazole, methfuroxam, metiram, metiram-zinc, metsulfovax, myclobutanil, neoasozin, nickel dimethyldithiocarbamate, nitrothai-iso-propyl, nuarimol, ofurace, organomercury compounds, oxadixyl, oxolinic acid, oxycarboxin, pefurazoate, penconazole, pencycuron, phenazin oxide, phosetyl-Al, phosphorus acids, phthalide, polyoxin D, polyram, probenazole, prochloraz, procymidone, propamocarb, propamocarb hydrochloride, propiconazole, propineb, propionic acid, prothiocarb, pyracarbolid, pyrazophos, pyrifenox, pyrimethanil, pyroquilon, pyroxyfur, pyrrolnitrin, quaternary ammonium compounds, quinconazole, quinomethionate, quintozene, rabenazole, sodium pentachlorophenate, streptomycin, sulphur, SSF-126, tebuconazole, techlofthalam, tecnazene, tetraconazole, thiabendazole, thicyofen, thifluzamide, 2-(thiocyanomethylthio)benzothiazole, thiophanate-methyl, thiram, timibenconazole, tolclofos-methyl, tolylfluanid, triacetate salt of 1,1'-iminodi(octamethylene)diguanidine, triadimefon, triadimenol, triazbutyl, triazoxide, tricyclazole, tridemorph, triforine, triflumizole, triticonazole, validamycin A, vapam, vinclozolin, XRD-563, zineb and ziram. The compounds of general formula (I) can be mixed with soil, peat or other rooting media for the protection of plants against seed-borne, soil-borne or foliar fungal diseases.

The following Examples illustrate the invention. Throughout the Examples, the term 'ether' refers to diethyl ether, magnesium sulphate was used to dry solutions, and solutions were concentrated under reduced pressure. Reactions involving air or water sensitive intermediates were performed under an atmosphere of nitrogen and solvents were dried before use, where appropriate. Unless otherwise stated, chromatography was performed on a column of silica gel as the stationary phase. Where shown, infrared and NMR data are selective; no attempt is made to list every absorption in all cases. $^1$H NMR spectra were recorded using CDCl$_3$-solutions unless otherwise stated. The following abbreviations are used throughout:

DMF=N,N-dimethylformamide m.p.=melting point t=triplet

NMR=nuclear magnetic resonance ppm=parts per million q=quartet

IR=infrared s=singlet m=multiplier b.p.=boiling point d=doublet br=broad

THF=tetrahydrofuran ether=diethyl ether

EXAMPLE 1

This Example illustrates the preparation of (E),(E)-methyl 2-[2-(5-methyl-6-iso-propoxypyrimidin-4-yl-acetoximinomethyl)phenyl]-3-methoxypropenoate (Compound No. 735 of Table I).

A solution of 4-chloro-5-methyl-6-iso-propoxypyrimidine (6.82 g), (1-ethoxyvinyl)-tributyltin (13.19 g) and bis(triphenylphosphine)palladium (II) chloride (0.8 g) in DMF (25 ml) was heated at 80° C. for 8 hours. The reaction mixture was cooled to room temperature and potassium fluoride (300 ml of a 10% aqueous solution) was added. The resulting mixture was stirred for 1 hour then filtered through Hyflo supercel filter aid which was rinsed through with ether. The filtrate was extracted with ether (×2) and the combined extracts washed with brine, then dried, concentrated and chromatographed using hexane:tert-butylmethyl ether 1:1 as the eluant to give 1-ethoxyvinyl-1-(5-methyl-6-iso-propoxypyrimidin-4-yl), (5.11 g, 63% yield) as a clear oil; $^1$H NMR (270 MHz): 1.37(9H,m); 2.17(3H,s); 3.95(2H, q); 4.47(1H,d); 4.53(1H,d); 5.38(1H,m); 8.56(1H,s)ppm.

A solution of 1-ethoxyvinyl-1-(5-methyl-6-iso-propoxypyrimidin-4-yl) (5.11 g) in acetone (150 ml) was treated with hydrochloric acid (6 ml of a 2M solution). The reaction mixture was allowed to stand for 16 hours and then concentrated. The residue was diluted with water and neutralised with sodium bicarbonate. The aqueous phase was extracted with ether (×2) and the combined extracts concentrated to give 4-acetyl-5-methyl-6-iso-propoxypyrimidine (3.92 g, 88% yield) as a yellow oil; $^1$H NMR (270 MHz): 1.39(6H,d); 2.30(3H,s); 2.65(3H,s); 5.40 (1H,m); 8.64(1H,s) ppm.

A solution of 4-acetyl-5-methyl-6-iso-propoxypyrimidine (3.92 g), hydroxylamine (1.58 g) and sodium acetate (1.5 g) in a 2:1 mixture of ethanol:water (30 ml) was heated to reflux then allowed to stand. The reaction was then poured into water and extracted with ethyl acetate. The combined extracts were dried, concentrated and chromatographed using ethyl acetate:hexane 2:3 as the eluant to give two fractions:

A. E-4-acetyl-5-methyl-6-iso-propoxypyrimidine oxime as a white solid (1.69 g, 40% yield) m.p. 95.4°–96.5° C.; $^1$H NMR (270 MHz): 1.27(6H,d); 2.07(3H,s); 2.12(3H,s); 5.28 (1H,m); 8.55(1H,s); 11.55(1H,s)ppm.

B. Z-4-acetyl-5-methyl-6-iso-propoxypyrimidine oxime as a white solid (1.7 g, 40% yield) m.p. 126.8°–127.7° C.; $^1$H NMR (270MHz): 1.28(6H,d); 1.87(3H,s); 1.98(3H,s); 5.28(1H,m); 8.55(1H,s); 10.77(1H,s)ppm.

A solution of E-4-acetyl-5-methyl-6-iso-propoxypyrimidine oxime (1.69 g) in DMF (10 ml) was added dropwise to a stirred suspension of sodium hydride (0.19 g) in DMF (20 ml). Two hours later, a solution of (E)-methyl 2-[2-(bromomethyl)phenyl]-3-methoxypropenoate (2.31 g) in DMF (10 ml) was added dropwise. After a further 2 hours the mixture was poured into water and extracted with ether (×4). The organic extracts were washed with brine, dried, concentrated and chromatographed using ether as the eluant to give the title compound (2.17 g, 65% yield) as a white solid, m.p. 56.3°–58.3° C.; $^1$H NMR (270 MHz) 1.35(6H,d); 2.09(3H, s); 2.24(3H,s); 3.68(3H,s); 3.81(3H,s); 5.13(2H,s); 5.37(1H, m); 7.1–7.6(4H,m); 7.58(1H,s); 8.56(1H,s)ppm.

EXAMPLE 2

This Example illustrates the preparation of methyl 2-[2-(isoquinolin-1-yl-acetoximino-methyl)phenyl]-3-methoxypropenoate (Compound No. 703 of Table I).

A solution of 1-chloroisoquinoline (4.9 g), (1-ethoxyvinyl)-tributyltin (10.82 g) and bis (triphenylphosphine)palladium (II) chloride (0.75 g) in DMF (40 ml) was heated at 90° C. for 7 hours. The reaction mixture was cooled to room temperature and potassium fluoride (300 ml of a 10% aqueous solution) was added. The resulting mixture was stirred for 1 hour then filtered through Hyflo supercel filter aid which was rinsed through with ether. The filtrate was extracted with ether (×2) and the combined extracts washed with brine, then dried, concentrated and chromatographed using ethyl acetate:hexane 3:7 to give 1-ethoxyvinyl-1-isoquinoline (4.84 g, 81% yield) as a yellow oil; $^1$H NMR: 1.46(3H,t); 4.10(2H,q); 4.65(2H,dd); 7.5–8.4(5H,m); 8.52(1H,d) ppm.

A solution of 1-ethoxyvinyl-1-isoquinoline (4.84 g) in acetone (50 ml) was treated with hydrochloric acid (5 ml of a 2M solution). The reaction mixture was refluxed for 2 hours then concentrated. The residue was diluted with water and neutralised with sodium bicarbonate. The aqueous phase was extracted with ethyl acetate (×3) and the combined extracts concentrated to give 1-acetyl-isoquinoline (3.84 g, 91% yield) as a yellow oil; $^1$H NMR: 2.87(3H,s); 7.64–7.75 (2H,m); 7.79–7.89(2H,m); 8.59(1H,d); 8.96(1H,d) ppm.

A solution of 1-acetyl-isoquinoline (3.42 g), hydroxylamine (1.53 g) and sodium acetate (2.46 g) in a 3:1 mixture of methanol:water (80 ml) was heated to reflux for 8 hours then allowed to stand for 16 hours. The reaction mixture was then poured into water and extracted with ethyl acetate. The combined extracts were dried, concentrated and chromatographed using ethyl acetate:hexane 3:7 as the eluant to give 1-acetyl-isoquinoline oxime (1.87 g, 58% yield) as a white crystalline solid m.p. 154.4°–155.3° C.; $^1$H NMR: 2.50(3H, s); 7.58–7.73(3H,m); 7.85(1H,m); 8.55(1H,m); 8.57(1H,m); 8.66(1H,s) ppm.

A solution of 1-acetyl-isoquinoline oxime (0.74 g) in DMF (10 ml) was added dropwise to a stirred suspension of sodium hydride (0.19 g) in DMF (20 ml). Two hours later, a solution of (E)-methyl 2-[2(bromomethyl)phenyl]-3-methoxypropenoate (1.14 g) in DMF (10 ml) was added dropwise. After a further 2 hours the mixture was poured into water and extracted with ether (×3). The organic extracts were washed with brine, dried, concentrated and triturated with hexane and ether to give the title compound (0.58 g, 37% yield) as a white solid, m.p. 96.0°–98.2° C.; $^1$H NMR 2.46(3H,s); 3.64(3H,s); 3.78(3H,s); 5.24(2H,s); 7.1–7.8(8H,m); 7.60(1H,s); 8.36(1H,d); 8.52(1H,d) ppm.

EXAMPLE 3

This Example illustrates the preparation of methyl 2-[2-(isoquinolin-3-yl-acetoximino-methyl)phenyl]-3-methoxypropenoate (Compound No. 793 of Table I).

Methyl magnesium chloride (2.6 ml of a 3.0M solution in THF) was added dropwise to a solution of isoquinoline-3-carbonitrile at 0°–5° C. After the addition the reaction mixture was stirred at room temperature for 1 hour, then quenched with water. Hydrochloric acid (2M aqueous solution) was added to the reaction mixture until the aqueous phase was pH2. After stirring for 30 minutes the aqueous was neutralised with sodium bicarbonate (solid) and extracted with ether (×2). The combined extracts were washed with water, dried and concentrated to give a crystalline solid. Recrystalisation from hexane gave 3-acetyl-isoquinoline (0.55 g, 14% yield) as a pale yellow solid m.p. 84.4°–86.8° C. $^1$H NMR: 2.83(3H,s); 7.69–7.81(2H,m); 7.99(1H,m); 8.04(1H,m); 8.49(1H,m); 9.29(1H,s) ppm.

A solution of 3-acetyl-isoquinoline (0.65 g), hydroxylamine (0.29 g) and sodium acetate (0.47 g) in a mixture of methanol (20 ml) and water (3 ml) was heated to reflux for 1.5 hours. The reaction was then poured into water and extracted with ethyl acetate. The combined extracts were dried, concentrated and triturated with hexane to give 3-acetyl-isoquinoline oxime (0.63, 89% yield) as a white crystalline solid m.p. 135°–142° C.; $^1$H NMR: 2.50(3H,s); 7.61(1H,t); 7.70(1H,t); 7.87(1H,d); 7.99(1H,d); 8.11(1H,s); 9.28(1H,s) ppm.

A solution of 3-acetyl-isoquinoline oxime (2.97 g) in DMF (20 ml) was added dropwise to a stirred suspension of sodium hydride (0.67 g) in DMF (20 ml). Half an later, a solution of (M)-methyl 2-[2-(bromomethyl)phenyl]-3-methoxypropenoate (5.02 g) in DMF (20 ml) was added dropwise. After a further hour the mixture was poured into water and extracted with ether (×3). The organic extracts were washed with brine, dried concentrated and chromatographed using ethyl acetate:hexane 3:7 as the eluant to give the title compound (2.37 g, 38% yield) as a white solid, m.p. 95.6°–96.2° C.; $^1$H NMR: 2.45(3H,s); 3.69(3H,s); 3.82(3H,s); 5.26(2H,s); 7.1–8.0(8H,m); 7.60(1H,s); 8.18(1H,s); 9.25 (1H,s) ppm.

EXAMPLE 4

This Example illustrates the preparation of methyl 2-[2-(4-(pyrid-2-yl)-pyrimidin-2-yl-acetoximino-methyl)phenyl]-3-methoxypropenoate (Compound No. 786 of Table I).

Borontrifluoride diethyletherate (0.42 ml) was added to a mixture of trimethylorthoacetate (5.25 ml) and trimethylsyilyl cyanide (5 ml) at 0° C. The reaction mixture was allowed to warm to room temperature and then stirred for 3 hours. The mixture was diluted with ether and washed with sodium bicarbonate solution. The organic phase was dried and concentrated to give 2,2-dimethoxypropionitrile (4.06 g, 94% yield) as a pale yellow liquid. $^1$H NMR: 1.55(3H,s); 3.22(6H,s) ppm.

2,2-Dimethoxypropionitrile (10 g) was added to sodium methoxide solution (prepared by dissolving 4.7 g of sodium in 40 ml of dry methanol). The mixture was warmed to 50° C. for 4 hours, then cooled before solid carbon dioxide (5 g) was added. The resulting sodium carbonate was filtered off and the filtrate concentrated and distilled at 50°–60° C. 13 mm Hg to give methyl 2,2-dimethoxypropionyl imidate (2.9 g, 23% yield) as a clear oil. $^1$H NMR: 1.45(3H,s); 3.29(6H, s); 3.80(3H,s); 7.99(1H,s) ppm.

Methyl 2,2-dimethoxypropionyl imidate (3.35 g) and ammonium chloride (1.55 g) was refluxed in methanol (20 ml) for 6 hours. The reaction mixture was cooled, filtered and concentrated to give a gum which crystalised on trituration with hexane and ether to give 2,2-dimethoxypropionyl amidine hydrochloride (3.24 g, 66% yield) as a hygroscopic solid.

2,2-Dimethoxypropionylamidine hydrochloride (3.24 g) and t-(pyrid-2-yl)-3-N,N-dimethylamino-prop-2-enone (3.38 g) was refluxed for 1.5 hours in a solution of sodium ethoxide (prepared by dissolving 0.49 g of sodium in 30 ml of dry ethanol). The mixture was cooled, concentrated, diluted with water, then extracted with ethyl acetate (×3). The organic extracts were combined, dried, and concentrated to give 2-acetyl-4-(pyrid-2-yl)pyrimidine dimethylacetal (2.45 g, 52% yield) as an oil. $^1$H NMR: 1.80(3H,s); 3.38(6H,s); 7.41(1H,m); 7.88(1H, t); 8.30(1H,d); 8.60(1H, d); 8.72(1H,d); 8.98(1H,d) ppm.

A solution of 2-acetyl-4-(pyrid-2-yl)-pyrimidine dimethylacetal (0.2 g) in dioxane (8 ml) was treated with hydrochloric acid (1 ml of a 2M solution). The reaction mixture was refluxed for 1 hour then concentrated. The residue was diluted with water and neutralised with sodium bicarbonate. The aqueous phase was extracted with ethyl acetate (×2) and the combined extracts concentrated to give 2-acetyl-4-(pyrid-2-yl)-pyrimidine (0.12 g, 74% yield) as a buff coloured solid; $^1$H NMR: 2.89(3H,s); 7.47(1H,m); 7.91(1H, m); 8.52(1H,d); 8.63(1H,d); 8.78(1H,d); 9.06(1H,d) ppm.

A solution of 2-acetyl-4-(pyrid-2-yl)-pyrimidine (1.0 g), hydroxylamine (0.39 g) and sodium acetate (0.62 g) in a mixture of ethanol (10 ml) and water (2 ml) was heated to reflux for 1.5 hours. The reaction was then poured into water the precipitate filtered and washed with hexane to give 2-acetyl-4-(pyrid-2-yl)-pyrimidine oxime (0.98 g, 91% yield) as a white crystalline solid m.p. 196°–8° C.; $^1$H NMR: 2.50(3H,s); 7.42(1H,m); 7.88(1H,m); 8.30(1H,d); 8.59(1H, d); 8.74(1H,d); 8.90(1H,d); 10.85(1H,brs) ppm.

A solution of 2-acetyl-4-(pyrid-2-yl)-pyrimidine oxime (0.8 g) in DMF (10 ml) was added dropwise to a stirred suspension of sodium hydride (0.20 g) in DMF (5 ml). 1.5 hours later, a solution of (E)-methyl 2-[2-(bromomethyl)phenyl]-3-methoxypropenoate (1.05 g) in DMF (10 ml) was added dropwise. After a further 3 hours the mixture was poured into water and extracted with ethyl acetate (×3). The organic extracts were washed with brine, dried concentrated and chromatographed using ethyl acetate as the eluant to give the title compound (0.93 g, 61% yield) as a white solid, m.p. 88°–90° C.; $^1$H NMR :2.50(3H,s); 3.69(3H,s); 3.82 (3H,s); 5.36(2H,s); 7.18(1H,m); 7.35(2H,m); 7.42(1H,m); 7.59(1H,s); 7.60(1H,m); 7.89(1H,m); 8.31(1H,d); 8.58(1H, d); 8.74(1H,d); 8.96(1H,d) ppm.

EXAMPLE 5

This Example illustrates the preparation of methyl 2-[2-(4-[1,1-di-fluoroethyl]-pyrimidin-2-yl-acetoximino-methyl)phenyl]-3-methoxypropenoate (Compound No. 763 of Table I).

A solution of methyl 2-[2-(4-[2,2,2-trifluoroethoxy]-pyrimidin-2-yl-acetoximino-methyl)phenyl]-3-methoxypropenoate (35 g, prepared as in WO 92/18487, Example 11, Compound No. 417) and hydrochloric acid (20ml of a 2M aqueous solution) was refluxed in acetone for 4 hours. The reaction mixture was concentrated, neutralised with sodium bicarbonate and extracted with ethyl acetate. The combined organic extracts were washed with water, dried and concentrated to give a solid which was triturated with hexane and ether to give methyl 2-[2-(4-hydroxypyrimidin-2-yl-acetoximino-methyl)phenyl]-3-methoxypropenoate (21.8 g, 77% yield) as a white solid.

Methyl 2-[2-(4-hydroxypyrimidin-2-yl-acetoximino-methyl)phenyl]-3-methoxypropenoate (5 g) and phosphoryl chloride (30 ml) were heated to reflux for 30 minutes. The cooled reaction mixture was poured onto ice, stirred and extracted with ethyl acetate (×3). The combined extracts were washed with brine, dried, decolourised with charcoal, concentrated and chromatographed, using ether as the eluant to give methyl 2-[2-(4-chloroyrimidin-2-yl-acetoximino-methyl)phenyl]-3-methoxypropenoate (2.3 g, 44% yield, Compound No 711 of Table I) as a gum. $^1$H NMR given in Table II.

A solution methyl 2-[2-(4-chloropyrimidin-2-yl-acetoximino-methyl)phenyl]-3-methoxypropenoate (4.0 g), (1-ethoxyvinyl)tributyltin (4.6 g), bis(triphenylphosphine) palladium (II) chloride (0.2 g), tetraethylammonium-chloride (1.75 g), and potassium carbonate (1.46 g) in DMF (30 ml) was heated at 90° C. for 3 hours. The cooled reaction mixture was poured into water and extracted with ethyl acetate (×3). The combined extracts were washed with brine, dried, concentrated and chromatographed using ethyl acetate:hexane 1:1 as the eluant to give methyl 2-[2-(4-[1-ethoxyvinyl]-pyrimidin-2-yl-acetoximino-methyl)phenyl]-3-methoxypropenoate (2.09 g, 48% yield, Compound No 752 of Table I) as a white solid m.p. 94°–95° C. $^1$H NMR: 1.45(3H,t); 2.41(3H,s); 3.68(3H,s); 3.82(3H,s); 3.98(2H,q); 4.52(1H,d); 5.32(2H,s); 5.78(1H,s); 7.17(1H,m); 7.35(2H,m); 7.57(1H,d); 7.57(1H,m); 7.59(1H,s); 8.81(1H,d) ppm.

A solution of methyl 2-[2-(4-[1-ethoxyvinyl]-pyrimidin-2-yl-acetoximino-methyl)phenyl]-3-methoxypropenoate (1.14 g) and hydrochloric acid (2 ml of a 2M aqueous solution) in acetone (20 ml) was stirred for 3 hours. The reaction mixture was concentrated, neutralised with sodium bicarbonate and extracted with ethyl acetate. The combined extracts were washed with water, dried, concentrated and triturated with hexane to give methyl-[2-(4-acetyl-pyrimidin-2-yl-acetoximino-methyl)phenyl]-3-methoxypropenoate (0.87 g, 82% yield, Compound No 753 of Table I) as a white solid m.p. 104°–106° C. $^1$H NMR: 2.45(3H,s); 2.78(3H,s); 3.68(3H,s); 3.82(3H,s); 5.34(2H,s); 7.18(1H,m); 7.35(2H,m); 7.55(1H,m); 7.59(1H,s); 7.82(1H,d); 9.07(1H,d) ppm.

Diethylaminosulphur trifluoride (0.16 ml, DAST) was added to a solution of methyl 2-[2-(4-acetyl-pyrimidin-2-yl-acetoximino-methyl)phenyl]-3-methoxypropenoate (0.5 g) in dichloromethane (10 ml). The reaction mixture was heated to reflux for 1 hour then stood for 16 hours. A further portion of DAST (0.4 ml) was added and the reaction mixture refluxed for 7 hours. The cooled reaction mixture was poured into water and extracted with ethyl acetate. The combined organic extracts were washed with sodium bicarbonate (a saturated aqueous solution), and then with brine. They were then concentrated and chromatographed using ethyl acetate:hexane 1:1 as the eluant. This gave a pale yellow gum which solidified on trituration with hexane to give the title compound (0.143 g, 27% yield) as a white solid m.p. 96°–97° C. $^1$H NMR: 2.03(3H,t); 2.39(3H,s); 3.68(3H, s); 3.82(3H,s); 5.34(2H,s); 7.17(1H,m); 7.35(2H,m); 7.52 (1H,m); 7.57(1H,d); 7.58(1H,s); 8.89(1H,d) ppm.

EXAMPLE 6

This Example illustrates the preparation of methyl 2-[2-(4-chlorodifluoromethyl-5-methyl-pyrimidin-2-yl-acetoximino-methyl)phenyl]-3-methoxypropenoate (Compound No 819 of Table I).

Methyl 2-[2-phthalimido-oxymethyl phenyl]-3-methoxypropenoate (1.32 g, prepared as described in Example 4 of EP 0463488) was dissolved in methanol (15 ml) at room temperature, hydrazine hydrate (0.19 ml) was added and the resulting solution stirred for 2 hours. The white precipitate which formed was filtered off and the filtrate concentrated to give a white semi-solid. This solid was diluted with ether, the resulting insoluble solid filtered off and the filtrate concentrated to give methyl 2-[2-amino-oxymethylphenyl]-3-methoxypropenoate as a yellow oil which was used immediately in the next stage without further purification.

A mixture of the methyl 2-[2-amino-oxymethylphenyl]-3-methoxypropenoate, 2-acetyl-4-chloro-difluoromethyl-5-methyl-pyrimidine (0.53 g) and pyridine (2 drops) in methanol was stirred at room temperature for 24 hours. The reaction mixture was concentrated and the residue chromatographed using ether as the eluant, to give, after trituration with hexane, the title compound (0.52 g, 50% yield) as a pale yellow solid m.p. 110°–111° C. $^1$H NMR: 2.40 (3H,s); 2.55(3H,s); 3.70(3H,s); 3.85(3H,s); 5.35(2H,s); 7.2–7.60(4H,m); 7.60(1H,s); 8.80(1H,s) ppm.

EXAMPLE 7

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration immediately before use. The formulations (100 ppm active ingredient) were sprayed on to the foliage or applied to the roots of the plants in the soil. The sprays were applied to maximum retention and the root drenches to a final concentration equivalent to approximately 40 ppm a.i. in dry soil. Tween 20 was added to give a final concentration of 0.05% when the sprays were applied to cereals.

For most of the tests the compounds were applied to the soil (roots) or to the foliage (by spraying) one or two days before the plant was inoculated with the disease. An exception was the test on *Erysiphe graminis* in which the plants were inoculated 24 hours before treatment. Foliar pathogens were applied by spray as zoosporangial suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease level present (i.e. leaf area covered by actively sporulating disease) on each of the treated plants was recorded using the following assessment scale:

0=0% disease present
1=0.1–1% disease present

3=1.1–3% disease present

5=3.1–5% disease present

10=5.1–10% disease present

20=10.1–20% disease present

30=20.1–30% disease present

60=30.1–60% disease present

90=60.1–100% disease present

Each assessment was then expressed as a percentage of the level of disease present on the untreated control plants. This calculated value is referred to as a POCO (Percentage of Control) value. An example of a typical calculation is as follows:

Disease level on untreated control=90

Disease level on treated plant=30

$$POCO = \frac{\text{disease level on treated plant}}{\text{disease level on untreated control}} \times 100 = \frac{30}{90} \times 100 = 33.3$$

This calculated POCO value is then rounded to the nearest of the values in the 9-point assessment scale shown above. In this particular example, the POCO value would be rounded to 30. If the calculated POCO falls exactly mid-way between two of the points, it is rounded to the lower of the two values.

The results are shown in Table III.

TABLE III

| Compound No of (Table No) | Egt | Sn | Pr | Pv | Pil | Po | Tc | Vi |
|---|---|---|---|---|---|---|---|---|
| 694 | 0 | 0 | 0 | 0 | 0 | 0 | 0 | 0 |
| 695 | 0 | 0 | 0 | 0 | 90 | 0 | 0 | 0 |
| 696 | 0 | 10 | 0 | 0 | 90 | 5 | 0 | 0 |
| 697 | 0 | 0 | 0 | 0 | 1 | 0 | 0 | 0 |
| 698 | 0 | 0 | 0 | 0 | 10 | 0 | 0 | 0 |
| 699 | 0 | 0 | 0 | 0 | 0 | 0 | 0 | 0 |
| 700 | 0 | 0 | 0 | 0 | 20 | 0 | 0 | 0 |
| 701 | 0 | 30 | 0 | 0 | 30 | 0 | 0 | 0 |
| 702 | 90a | 90a | 90a | 0a | 90a | 60a | 90a | 90a |
| 703 | 0 | 0 | 0 | 0 | 5 | 3 | — | 0 |
| 704 | 0 | 0 | 0 | 0 | 30 | 1 | — | 3 |
| 705 | 90 | 90 | 30 | 0 | 90 | 90 | — | 30 |
| 706 | 3 | 0 | 90 | 0 | 60 | — | 60 | 0 |
| 707 | 0 | 0 | 0 | 0 | 90 | 1 | — | 0 |
| 708 | 0 | 0 | 0 | 0 | 10 | 0 | 60 | 0 |
| 709 | 0 | 0 | 0 | 0 | 0 | 5 | 0 | 0 |
| 710 | 0 | 0 | 0 | 0 | 0 | 0 | 0 | 0 |
| 711 | 10 | 30 | 60 | 0 | 5 | 0 | 30 | 0 |
| 712 | 0 | 30 | 90 | 0 | 0 | 0 | 90 | 0 |
| 713 | 0 | 0 | 0 | 0 | 0 | 0 | 0 | — |
| 714 | 0 | 0 | 0 | 0 | 5 | 0 | 0 | 90 |
| 715 | 0 | 0 | 0 | 0 | 5 | 0 | 0 | 90 |
| 716 | 0 | 30 | 0 | 5 | 90 | 20 | 90 | 0 |
| 717 | 0 | 0 | 0 | 0 | 0 | 0 | 20 | 0 |
| 718 | 30 | 90 | 0 | 0 | 90 | 20 | 90 | 0 |
| 719 | 0 | 0 | 0 | 0 | 0 | 0 | 60 | 0 |
| 721 | 90 | 0 | 90 | 0 | 90 | — | 0 | 5 |
| 722 | 90 | 90 | — | 0 | 0 | 60 | 60 | 90 |
| 723 | 0 | 0 | — | 0 | 1 | 0 | 0 | 0 |
| 724 | 30 | 20 | — | 0 | 20 | 0 | 30 | 0 |
| 725 | 0 | 0 | — | 0 | 30 | 0 | 0 | 0 |
| 726 | 0 | 0 | 0 | 0 | 0 | 0 | 0 | 0 |
| 727 | 0 | 0 | 0 | 0 | 30 | — | 0 | 0 |
| 728 | 0 | 0 | 0 | 0 | 30 | 0 | 0 | 0 |
| 729 | 0 | 0 | 0 | 0 | 5 | 0 | 0 | 0 |
| 730 | 0 | 3 | 0 | 0 | 30 | 0 | 20 | 0 |
| 732 | 0 | 0 | 0 | 0 | 90 | — | 0 | 0 |
| 733 | 0 | 0 | 0 | 0 | 30 | — | 0 | 0 |
| 734 | 20 | 0 | 10 | 10 | 90 | — | 90 | 10 |

TABLE III-continued

| Compound No of (Table No) | Egt | Sn | Pr | Pv | Pil | Po | Tc | Vi |
|---|---|---|---|---|---|---|---|---|
| 735 | 0 | 0 | 0 | 0 | 30 | 0 | 0 | 0 |
| 736 | 0 | 0 | 0 | 0 | 5 | 0 | 20 | 0 |
| 737 | 0 | 0 | 0 | 0 | 0 | 0 | 0 | 0 |
| 738 | 5 | 0 | 0 | 0 | 0 | 0 | 0 | 0 |
| 739 | 0 | 0 | 0 | 0 | 0 | — | 5 | 0 |
| 740 | 0 | 0 | 0 | 0 | 0 | 0 | 0 | 0 |
| 741 | 60 | 30 | 90 | 0 | 60 | 10 | 90 | 0 |
| 742 | 10 | 90 | 90 | 90 | 90 | 20 | 30 | 90 |
| 743 | 0 | 10 | 0 | 0 | 20 | 0 | 0 | 0 |
| 744 | 20 | 10 | 10 | 0 | 0 | 3 | — | 0 |
| 745 | 0 | 0 | 0 | 0 | 0 | — | 0 | 0 |
| 746 | 3 | 0 | 90 | 0 | 60 | — | 60 | 0 |
| 747 | 0 | 0 | 0 | 0 | 5 | — | 0 | 0 |
| 748 | 0 | 0 | 0 | 0 | 90 | — | 0 | 0 |
| 750 | 0 | 0 | 0 | 0 | 0 | 0 | 0 | 0 |
| 751 | 0 | 0 | 0 | 0 | 10 | 0 | 0 | 0 |
| 752 | 0 | 0 | 0 | 0 | 0 | 0 | 0 | 0 |
| 753 | 0 | 0 | 0 | 0 | 60 | 0 | 30 | 0 |
| 754 | 0 | 0 | 0 | 0 | 90 | — | 5 | 0 |
| 755 | 0 | 30 | 0 | 0 | 10 | — | 60 | 0 |
| 756 | 0 | 0 | 0 | 0 | 90 | 0 | 0 | 0 |
| 757 | 0 | 0 | 0 | 0 | 0 | 0 | 0 | 0 |
| 758 | 0 | 0 | 0 | 0 | 0 | 0 | 0 | 0 |
| 759 | 0 | 0 | 0 | 0 | 5 | 0 | 0 | 0 |
| 760 | 0 | 0 | — | 0 | 90 | — | 0 | 0 |
| 761 | 30 | 10 | — | 0 | 10 | — | 5 | 0 |
| 762 | 0a | 90a | — | 30a | 90a | 30a | — | 30a |
| 763 | 0 | 0 | — | 0 | 0 | — | 0 | 0 |
| 764 | 0 | 20 | 0 | 0 | 20 | 0 | 0 | 0 |
| 765 | 0 | 0 | 0 | — | 0 | 0 | 0 | 0 |
| 766 | — | 90 | 0 | 0 | 20 | — | 90 | 20 |
| 767 | — | 0 | 0 | 0 | 10 | — | 0 | 0 |
| 768 | — | 90 | 90 | 0 | 5 | — | 90 | 20 |
| 769 | 0 | — | 0 | 0 | 0 | — | 0 | — |
| 770 | 1 | 0 | — | 0 | 0 | — | 0 | 0 |
| 771 | — | 90 | 90 | 3 | 10 | — | 30 | 0 |
| 772 | — | 90 | 60 | 3 | 30 | — | 90 | 0 |
| 773 | 0a | 60a | 10a | 30a | 90a | 0a | 60a | 0a |
| 774 | 60 | 0 | 0 | — | 0 | 1 | 0 | 0 |
| 775 | 90 | 0 | 90 | 0 | 10 | 20 | 5 | 10 |
| 776 | 10 | 0 | 0 | 0 | 5 | 1 | 0 | 0 |
| 777 | 0 | 0 | 0 | 0 | 0 | 0 | 0 | 0 |
| 778 | 0 | 20 | 0 | 0 | 0 | 5 | 30 | 0 |
| 779 | 90a | 90a | 0a | 20a | 60a | 90a | 5a | 0a |
| 780 | 30 | 60 | 90 | 0 | 5 | 60 | — | 5 |
| 781 | 90 | 60 | 90 | 90 | 90 | 90 | — | 60 |
| 782 | 90 | 60 | 90 | 60 | 60 | 60 | — | 30 |
| 783 | 0 | 0 | 0 | 0 | 10 | 0 | — | 0 |
| 784 | 5 | 0 | 0 | 0 | 0 | — | — | 0 |
| 785 | 90 | 20 | 90 | 0 | 20 | 0 | — | 0 |
| 786 | 0 | 0 | 0 | 0 | 0 | 0 | — | 0 |
| 787 | 0 | 3 | 1 | 0 | 0 | 0 | — | 0 |
| 788 | 0 | 0 | 0 | 0 | 0 | 0 | 0 | 0 |
| 789 | 0 | 0 | 0 | 0 | 0 | 0 | 0 | 0 |
| 790 | 0 | 0 | 0 | 0 | 0 | 0 | 0 | — |
| 791 | 90 | 60 | 90 | 10 | 90 | 60 | 30 | — |
| 792 | 90 | 0 | 0 | 0 | 30 | — | 0 | 0 |
| 793 | 0 | 0 | 0 | 0 | 0 | — | 0 | 0 |
| 794 | 90 | 90 | 60 | 0 | 90 | — | 90 | 0 |
| 795 | 0 | 0 | 0 | 0 | 0 | — | 0 | 0 |
| 796 | 0 | 0 | 0 | 0 | 3 | — | 0 | 0 |
| 797 | 30 | 3 | 10 | 0 | 3 | 60 | 0 | 0 |
| 798 | 90 | 10 | 90 | 5 | 10 | 90 | 5 | 5 |
| 799 | 90a | 0a | 90a | 0a | 90a | 0a | 5a | 5a |
| 800 | 90a | 1a | 0a | 0a | — | 0a | 60a | 0a |
| 801 | 0 | — | 0 | 0 | 0 | 0 | 0 | 0 |
| 802 | 0 | 90 | 0 | 0 | 1 | — | 0 | 0 |
| 803 | 0 | 60 | 0 | 0 | 60 | 0 | 0 | 0 |
| 804 | 0 | 0 | 0 | 0 | 0 | 0 | 0 | 0 |
| 805 | 0 | 0 | 5 | 0 | 0 | 0 | 90 | 0 |
| 807 | 20 | 5 | — | 0 | 0 | — | 0 | 0 |
| 808 | 10 | 0 | 1 | 0 | 0 | 0 | 0 | 0 |
| 809 | 0 | 0 | 0 | 0 | 0 | 0 | 0 | 0 |
| 810 | 30 | 0 | 0 | 0 | 0 | — | — | 0 |

TABLE III-continued

| Compound No of (Table No) | Egt | Sn | Pr | Pv | Pil | Po | Tc | Vi |
|---|---|---|---|---|---|---|---|---|
| 811 | 20 | 0 | 0 | 0 | 0 | 1 | — | 0 |
| 812 | 0 | 0 | 0 | 0 | 0 | 3 | 0 | — |

Unless stated otherwise, data represent activity following application as a combined foliar spray and root drench treatment at 100 ppm.

a 10 ppm foliar application only
—No result

Key to Diseases

Pr *Puccinia recondita* Tc *Thanetophorus cucumeris*
Egt *Erysiphe graminis tritici* Vi *Venturia inaequalis*
Sn *Septoria nodorum* Pv *Plasmopara viticola*
Po *Pyricularia oryzae* Pil *Phytophthora infestans lycopersici*

CHEMICAL FORMULAE
(IN DESCRIPTION)

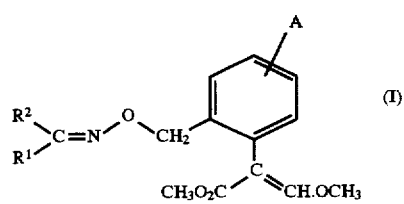

Compound No. 743 from Table I

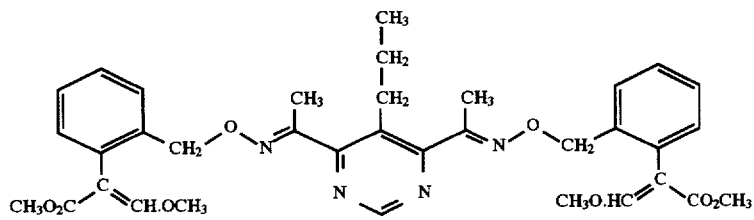

Compound No. 744 from Table I

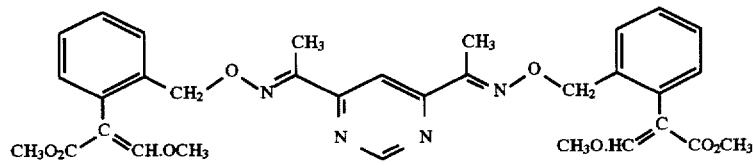

Compound No. 734 from Table I

Compound No. 760 from Table I

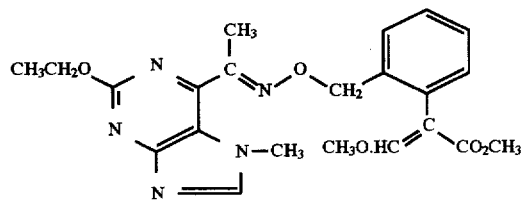

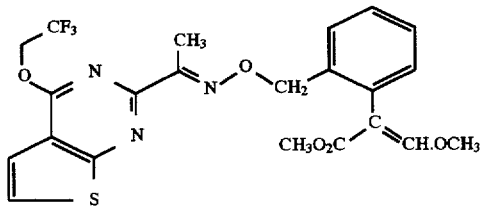

Compound No. 761 from Table I

Compound No. 772 from Table I

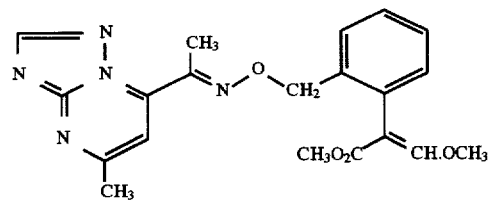

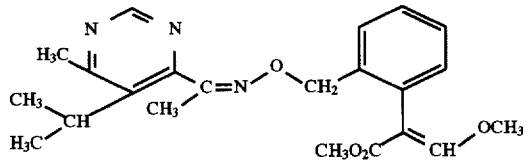

Compound No. 799 from Table I
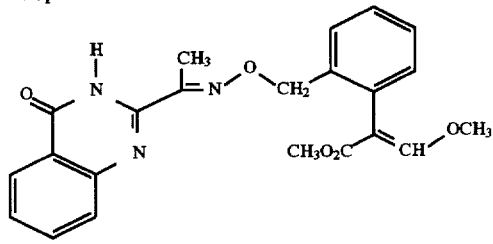
Scheme I
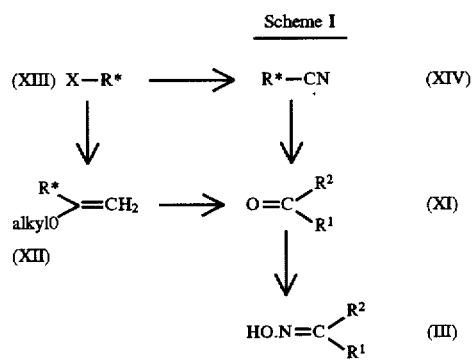
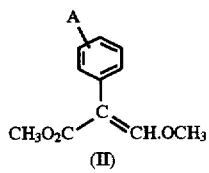
-continued
Scheme I
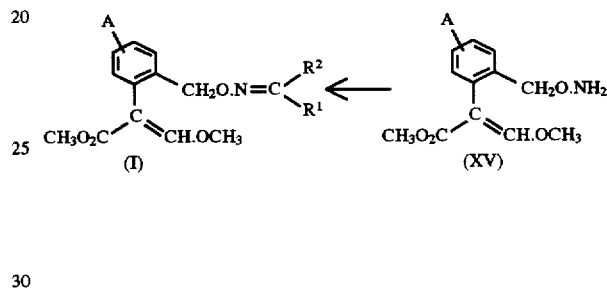
Scheme 2
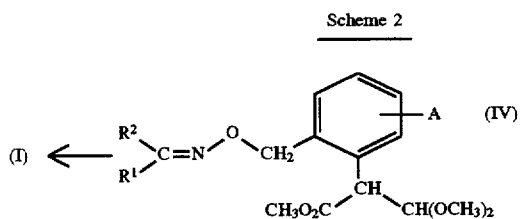

-continued
Scheme 2

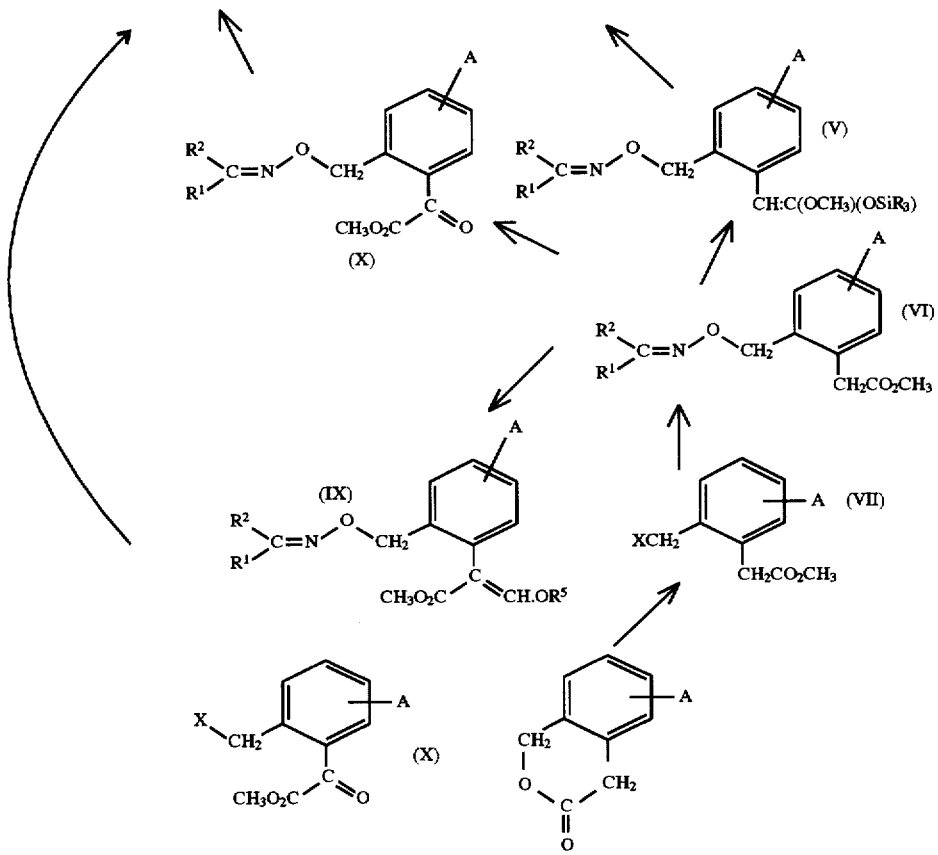

We claim:
1. A compound of formula (I):

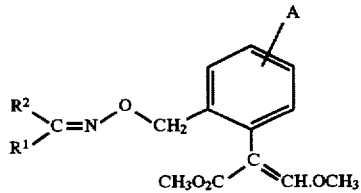

wherein A is hydrogen, halogen, hydroxy, $C_{1-4}$ alkyl, $C_{1-4}$ alkoxy, $C_{1-4}$ haloalkyl, $C_{1-4}$ haloalkoxy, $C_{1-4}$ alkylcarbonyl, $C_{1-4}$ alkoxycarbonyl, phenoxy, nitro or cyano; and one of $R^1$ and $R^2$ is hydrogen, $C_{1-4}$ alkyl, $C_{1-4}$ haloalkyl, halogen or cyano while the other is isoquinoline optionally substituted with one or more of the following: halogen, hydroxy, mercapto, $C_{1-4}$ alkyl, $C_{2-4}$ alkynyl, $C_{2-4}$ alkenyl, $C_{1-4}$ alkoxy, $C_{2-4}$ alkenyloxy, $C_{2-4}$ alkynyloxy, halo ($C_{1-4}$)alkyl, halo ($C_{1-4}$) alkoxy, $C_{1-4}$ alkylthio, halo($C_{1-4}$)alkylthio, hydroxy ($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, methylenedioxy (optionally substituted with fluorine or $C_{1-4}$ alkyl), aryl, heteroaryl, aryloxy, heteroaryloxy, aryl($C_{1-4}$)alkyl (in which the alkyl moiety is optionally substituted with hydroxy), heteroaryl($C_{1-4}$)alkyl, aryl($C_{2-4}$)alkenyl, heteroaryl ($C_{2-4}$)alkenyl, aryl($C_{1-4}$)alkoxy, heteroaryl($C_{1-4}$)alkoxy, aryloxy($C_{1-4}$)alkyl, hereroaryloxy($C_{1-4}$)alkyl, $C_{1-4}$; alkanoyloxy, benzolyloxy, cyano, thiocyanato, nitro, —NR'R", —NHCOR', —NHCONR'R", —CONR'R", —COOR', —OSO$_2$R', —SO$_2$R'—COR', —CR'=NR" or —N=CR'R"; wherein the aryl or heteroaryl rings of any of the foregoing substituents are optionally substituted by one or more of the following: halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$)alkoxy, $C_{1-4}$ alkylthio, hydroxy ($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, alkanoyloxy, benzoyloxy, cyano, thiocyanato, nitro, —NR'R", —NHCOR', —NHCONR'R", —CONR'R", —COOR', —SO$_2$R', —OSO$_2$R', —COR', —CR'=NR" or —N=CR'R"; R' and R" are independently hydrogen, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy; aryl is phenyl or naphthyl; and heteroaryl is pyridinyl, pyrimidinyl, pyridazinyl, pyrazinyl, triazinyl (1,2,3-, 1,2,4- or 1,3,5-), furyl, thienyl, pyrrolyl, pyrazolyl, imidazolyl, triazolyl (1,2,3- or 1,2,4-), oxazolyl, isoxazolyl, thiazolyl, isothiazolyl, quinolinyl, isoquinolinyl, cinnolinyl, quinazolinyl, quinoxalinyl, indolinyl, isoindolinyl, benzofuranyl, benzothienyl or benzimidazolinyl.

2. A compound of formula (I) as claimed in claim 1, wherein A is hydrogen, $R^2$ is methyl and $R^1$ is isoquinoline unsubstituted or substituted by one or more of halogen, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ haloalkylthio, $C_{1-4}$ hydroxyalkyl, $C_{1-4}$ alkoxy ($C_{1-4}$)alkyl, $C_{1-4}$ alkoxy($C_{1-4}$)alkoxy($C_{1-4}$)alkyl, nitro, cyano, COR', NR'R", OCOR', hydroxy, mercapto, $C_{2-4}$ alkenyl, $C_{2-4}$ alkynyl, $C_{2-4}$ alkenyloxy, $C_{2-4}$ alkynyloxy, $C_{3-6}$ cycloalkyl, $C_{3-6}$ cycloalkyl($C_{1-4}$)alkyl, NHCOR' or CONR'R"; R' and R" are, independently, hydrogen, $C_{1-4}$ alkyl, $C_{1-4}$ alkoxy, $C_{1-4}$ alkylthio, $C_{3-6}$ cycloalkyl or $C_{3-6}$ cycloalkyl($C_{1-4}$)alkyl or phenyl, phenoxy, benzyl or benzyloxy, the aromatic parts of which are optionally substituted by halogen, $C_{1-4}$ alkyl or $C_{1-4}$ alkoxy.

3. A compound of formula (I) as claimed in claim 1, wherein A is hydrogen, $R^2$ is methyl and $R^1$ is isoquinoline unsubstituted or substituted by one or more of halogen, $C_{1-4}$ alkyl, $C_{1-4}$ alkoxy, $C_{1-4}$ haloalkyl or $C_{1-4}$ haloalkoxy.

4. A process for preparing a compound of formula (I) which comprises

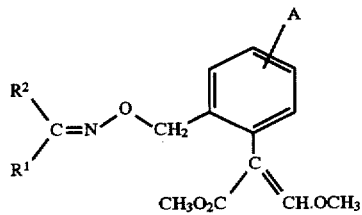

(I)

a) reacting a compound of formula (II)

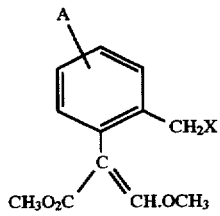

(II)

wherein X is a leaving group, with the salt of an oxime of formula (III)

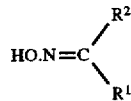

(III)

under basic conditions; or b) treating a compound of formula (XV):

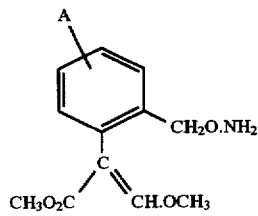

(XV)

with a compound of formula (XI):

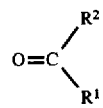

(XI)

or c) treating a compound of formula (IX):

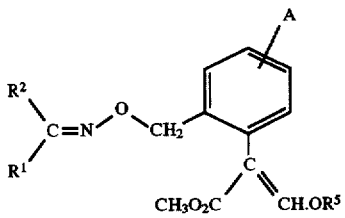

(IX)

with a compound of $CH_3L$; or d) eliminating the elements of methanol from a compound of formula (IV):

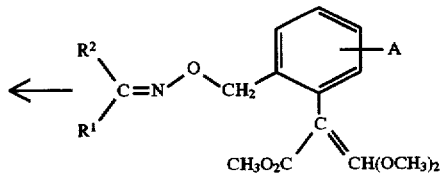

(IV)

under acidic or basic conditions; or e) treating a ketoester of formula (X):

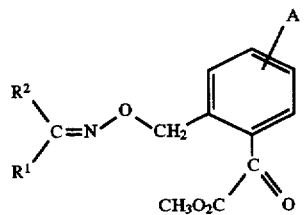

(X)

with a methoxymethylenation reagent;
wherein L is a leaving group, $R^5$ is a metal atom, A is hydrogen, halogen, hydroxy, $C_{1-4}$ alkyl, $C_{1-4}$ alkoxy, $C_{1-4}$ haloalkyl, $C_{1-4}$ haloalkoxy, $C_{1-4}$ alkylcarbonyl, $C_{1-4}$ alkoxycarbonyl, phenoxy, nitro or cyano; and one of $R^1$ and $R^2$ is hydrogen, $C_{1-4}$ alkyl, $C_{1-4}$ haloalkyl, halogen or cyano while the other is isoquinoline optionally substituted with one or more of the following: halogen, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$)alkoxy, $C_{1-4}$ alkylthio, halo($C_{1-4}$)alkylthio, hydroxy($C_{1-4}$)alkyl, $C_{1-4}$ alkoxy($C_{1-4}$)alkyl, $C_{3-6}$ cycloalkyl, $C_{3-6}$ cycloalkyl ($C_{1-4}$) alkyl, methylenedioxy (optionally substituted with fluorine or $C_{1-4}$ alkyl), aryl, heteroaryl, aryloxy, heteroaryloxy, aryl($C_{1-4}$)alkyl (in which the alkyl moiety is optionally substituted with hydroxy), heteroaryl ($C_{1-4}$)alkyl, aryl($C_{2-4}$)alkenyl, heteroaryl($C_{1-4}$)alkenyl, aryl($C_{1-4}$)alkoxy, heteroaryl($C_{1-4}$)alkoxy, aryloxy($C_{1-4}$) alkyl, heteroaryloxy($C_{1-4}$)alkyl, acyloxy, cyano, thiocyanato, nitro, —NR'R", —NHCOR', —NHCONR'R", —CONR'R", —COOR', —OSO$_2$R', —SO$_2$R', —COR', —CR'=NR" or —N=CR'R"; wherein the aryl or heteroaryl rings of any of the foregoing substituents are optionally substituted by one or more of the following: halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$)alkoxy, $C_{1-4}$ alkylthio, hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, alkanoyloxy, benzoyloxy, cyano, thiocyanato, nitro, —NR'R", —NHCOR', —NHCONR'R", —CONR'R", —COOR', —SO$_2$R', —OSO$_2$R', —COR', —CR'=NR" or —N=CR'R"; R' and R" are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy; aryl is phenyl or naphthyl; and heteroaryl is pyridinyl, pyrimidinyl, pyridazinyl, pyrazinyl, triazinyl (1,2,3-, 1,2,4- or 1,3,5-), furyl, thienyl, pyrrolyl, pyrazolyl, imidazolyl, triazolyl (1,2,3- or 1,2,4-), oxazolyl, isoxazolyl, thiazolyl, isothiazolyl, quinolinyl, isoquinolinyl, cinnolinyl, quinazolinyl, quinoxalinyl, indolinyl, isoindolinyl, benzofuranyl, benzothienyl or benzimidazolinyl.

5. A fungicidal composition comprising, as an active ingredient, a compound as claimed in claim 1 and a fungicidally acceptable carrier or diluent therefor.

6. A process for combating fungi which comprises applying to a plant, to a seed of a plant or to the locus thereof, a fungicidally acceptable amount of a compound as claimed in claim 1.

7. A process for combating fungi which comprises applying to a plant, to a seed of a plant or to the locus thereof, a fungicidally effective amount of a composition as claimed in claim 5.

* * * * *